(12) United States Patent
John

(10) Patent No.: US 12,171,968 B2
(45) Date of Patent: Dec. 24, 2024

(54) SYSTEM FOR DISPENSING CONTROLLED AND SELECTED CONCENTRATIONS OF CHEMICAL SALT COMPOSITIONS

(71) Applicant: Vlada John, Larchmont, NY (US)

(72) Inventor: Vlada John, Larchmont, NY (US)

( * ) Notice: Subject to any disclaimer, the term of this patent is extended or adjusted under 35 U.S.C. 154(b) by 213 days.

(21) Appl. No.: 17/451,237

(22) Filed: Oct. 18, 2021

(65) Prior Publication Data
US 2022/0032024 A1 Feb. 3, 2022

Related U.S. Application Data

(63) Continuation-in-part of application No. 16/284,357, filed on Feb. 25, 2019, now Pat. No. 11,148,104.

(60) Provisional application No. 62/635,042, filed on Feb. 26, 2018.

(51) Int. Cl.
| | |
|---|---|
| *A61M 35/00* | (2006.01) |
| *B05B 1/18* | (2006.01) |
| *B05B 7/24* | (2006.01) |
| *B05B 15/628* | (2018.01) |

(52) U.S. Cl.
CPC ............... *A61M 35/00* (2013.01); *B05B 1/18* (2013.01); *B05B 7/2462* (2013.01); *B05B 15/628* (2018.02); *A61M 2205/7545* (2013.01)

(58) Field of Classification Search
CPC .. B05B 1/16; B05B 1/169; B05B 1/18; B05B 7/2443; B05B 7/2462; B05B 15/628; E03C 1/046; E03C 1/0465
USPC ................ 239/310, 312, 315, 316, 317, 562
See application file for complete search history.

(56) References Cited

U.S. PATENT DOCUMENTS

| | | | | |
|---|---|---|---|---|
| 1,973,319 | A * | 9/1934 | Nelson | E03C 1/0465 239/315 |
| 2,202,001 | A * | 5/1940 | Gudmundsen | C02F 1/002 383/29 |
| 2,485,112 | A * | 10/1949 | Rose | B05B 7/2462 239/314 |
| 3,018,969 | A * | 1/1962 | Gentry | B05B 7/1418 239/443 |
| 3,157,320 | A * | 11/1964 | Sherriffe | A47K 5/14 222/251 |
| 4,081,139 | A * | 3/1978 | Migliozzi | B05B 7/2462 211/115 |
| 5,181,533 | A * | 1/1993 | Kooi | B01F 21/15 422/275 |
| 5,274,858 | A * | 1/1994 | Berry | A47K 5/08 4/605 |

(Continued)

*Primary Examiner* — Cody J Lieuwen
(74) *Attorney, Agent, or Firm* — Rosenberg, Klein & Lee

(57) ABSTRACT

A chemical salt composition dispensing system for dispensing controlled concentrations of aqueous chemical salt compositions to a user includes an outer housing having proximal and distal ends. The outer housing includes a base member located at the distal end of the outer housing. A sieve member is releasable to and insertable into the outer housing member. A spatially adjustable positioning member is connected to the outer housing and is flexibly secured to a shower head for positioning the outer housing and the sieve member at a selected distance between a user and the shower head. The dispensing system includes a flow control mechanism connected to the base member and is manually operated by the user to control the flow rate of the aqueous chemical composition dispensed to the user.

29 Claims, 17 Drawing Sheets

(56) References Cited

U.S. PATENT DOCUMENTS

| | | | | |
|---|---|---|---|---|
| 5,779,154 A | * | 7/1998 | Martin | B05B 7/2462 239/315 |
| 8,800,891 B2 | * | 8/2014 | Cheng | E03C 1/046 239/525 |
| 2009/0101733 A1 | * | 4/2009 | Popov | B05B 1/1636 4/615 |
| 2010/0206799 A1 | * | 8/2010 | Leavitt | C02F 1/002 210/314 |
| 2016/0214125 A1 | * | 7/2016 | Hextall | B05B 1/16 |

* cited by examiner

SYSTEM FOR DISPENSING CONTROLLED AND SELECTED CONCENTRATIONS OF CHEMICAL SALT COMPOSITIONS

REFERENCES TO RELATED APPLICATIONS

This application is a continuation in part of application Ser. No. 16/284,357 filed Feb. 25, 2019, now U.S. Pat. No. 11,148,104 issued on 19 Oct. 2021 which claims priority to and is based upon Provisional Application Ser. No. 62/635,042 filed on 26 Feb. 2018.

FIELD OF THE INVENTION

This invention is directed to the field of promoting wellness and personal care. This invention is further directed to the transdermal application of controlled and selective amounts of chemical salt compositions to the human body. Still further this invention is directed to the field of chemical salt composition dispensing systems for transdermal application to the body of a user. In particular, this invention relates to the field of providing dispensing systems for chemical salt compositions where hydroxide ions are transdermally applied to the body of a user. More in particular this invention is directed to the field of dispensing Magnesium Sulfate, commonly referred to as Epsom salts which produces hydroxide ions when dissolved in water. Still further, this invention relates to the technology of dispensing chemical salt compositions through the dermal layer of a user for promoting health and well-being benefits where the ions may enter the body through the skin of the user. More in particular, this invention relates to applying selective amounts of chemical salt compositions to the body of the user for aiding in exfoliation and promotion of new skin cell growth. Further this invention relates to the field of dispensing chemical salt compositions of controlled concentrations at a controlled rate and within specified time interval ranges. The time range may be adjusted to obtain an improved effect of the transdermal application of the chemical salt compositions to the user's body. The invention is further directed to the field of chemical salt composition dispensing systems where the chemical salt fluid mixture can be maintained in a container in combination with essential oil solutions or other sources of fragrance and then dispensed at a controlled rate to the body of a user. This invention is directed to the field of providing a dispensing system which has user friendly features such as being easily collapsible, lightweight, and/or transportable.

BACKGROUND OF THE INVENTION

Chemical salts are ionic compounds which can be formed by the neutralization reaction of an acid and a base. Chemical salts are composed of related number of cations so that the overall product is electrically neutral without a net charge. Such chemical salt compositions may be inorganic or organic. Epsom salt is commonly known as magnesium sulfate and has three differing forms, such as a heptahydrate, anhydrous and monohydrate form. The chemical compound includes sulfur/magnesium/oxygen. In its hydrate form, Epsom salt has a monoclinic crystal structure and the hydrate state is generally used for solution preparation, especially in medical preparations. Epsom salts appear similar to standard table salt, however, in medicinal use such is generally provided in larger salt crystals for use in, for example, bath water.

Numerous benefits for health/well-being have been reported with respect to positive effects of magnesium in Epsom salt. The Epsom salt breaks down into magnesium and sulfate with proponents of the practice believing that when a person soaks in an Epsom bath, the ions enter into the body transdermally or otherwise provide benefits.

There is support for the claim that both magnesium and sulfate ions, which are formed when magnesium sulfate is dissolved in water, can be transported through the skin. Transdermal application of such chemical salt compositions is thought to aid in a number of areas such as relief for stress and promotion of sleep.

Chemical salt compositions and, in particular, Epsom salts, are considered to be a good exfoliator for skin and when applied to the skin, such provides benefits such as decreasing acne, increasing hydration, balancing or adjusting chemical parameters within the body. The use of Epsom salts are believed to aid in exfoliation and promotion of new skin cell growth which allows skin to become softer to the touch and generally have a better tactile feel.

Other types of chemical salt compositions are known to be used in baths and for skin including various sea salts and botanicals. Himalayan salt mixtures may include, for example, calcium, magnesium, potassium, copper and iron.

PRIOR ART

Chemical salt compositions such as Epsom salts are believed to provide beneficial results in improving the health of users. In prior art uses of Epsom salts, the chemical salt compositions have been generally put into bath water to permit the user to bathe in the presence of an aqueous solution of chemical salt compositions and water. However the use of Epsom salts simply being inserted into bath water does not permit a controlled amount of the Epsom salts to be transdermally passed into the user's body. Additionally the use of Epsom salts in bath water does not permit the interfacing of the Epsom salts or other chemical salt compositions to be interfaced with the user's body for a specified time interval to obtain the maximum effects of the salt ions.

Additionally, when chemical salt compositions are used in conjunction with a bathtub containing both the water and the chemical salt composition, the amount of salt will be much less than the amount of water and/or the user must use large amounts of salt to obtain higher concentrations of the mixture such as saturated or supersaturated levels.

Additionally when chemical salt compositions are used in conjunction with a bathtub containing both the water and the chemical salt composition, it is impossible to target specific areas of the user's body which will benefit the most from the salt ions introduced transdermally.

There are no known chemical salt dispensing mechanisms which are adapted to be used in conjunction with a standard shower head to permit a controlled amount of chemical salt composition to be pre-mixed to a desired concentration, which may only rely upon gravity for dispensing, which permit the user to easily determine when the salt mixture is used up, or to provide various other benefits for providing the mixture so that benefits may be obtained, for example, such as enabling ions to be transdermally passed into a user's body while the user is taking a shower.

Thus, there is a long felt need to provide a dispensing system which can contain a specific amount of a chemical salt solution and dispense such in a controlled manner with respect to flow rate, and to largely or fully dissociate the rate of dispensing the solution from the concentration of the solution, and the amount of chemical salt solution being applied during a specified time interval.

SUMMARY OF THE INVENTION

This invention relates to a dispensing system for dispensing salt solutions transdermally to the human body.

The subject invention is directed to the system for dispensing controlled and selective amounts (e.g., volumes and concentrations) of chemical salt compositions to the human body. In embodiments, the system includes a tubular container extending in a vertical direction having a proximal end and a distal end. The tubular container includes a side wall extending between the distal and proximal ends of the tubular container. At least a first sieve member or shelf member is mounted to a side wall of the tubular container between the distal end and the proximal end of the tubular container. The first sieve or shelf member has a plurality of through openings passing there through and is mounted within the tubular container below a salt composition chamber formed within the tubular container between the first sieve or shelf member and the proximal end of the tubular container for containment of a chemical salt composition.

In an embodiment, at least a second sieve or shelf member is mounted to the side wall of the tubular container below the first sieve or shelf member defining a mixing flow chamber and having a number or plurality of second sieve or shelf through openings passing through the second sieve or shelf member. In the overall concept of the dispensing system, such includes a first chemical salt composition chamber above a first sieve or shelf member and a second mixing flow chamber below the first sieve member and above a second sieve member for permitting mixtures of water and chemical salt compositions to flow out of the dispensing system onto the body of a user at a predetermined rate.

In embodiments, both the first sieve or first shelf member and the second sieve or second shelf member of the dispensing system include respective through openings where the number of through opening of the first shelf member is less than the number of openings of the second shelf member.

An object of the subject dispensing system is to provide a source of chemical salt compositions and in particular Epsom salt solutions along with possible essential oils to be applied to a user which permits the user to have a higher and/or a controllable concentration of Epsom salt applied to the body than would occur in a bathtub which includes the bath water, possible essential oils and the chemical salt composition.

Still further, it is an object of the subject system to provide a source of Epsom salts to the body of the user in a controlled manner at a controllable rate of flow.

It is a further object of the subject system to provide a source of chemical salt compositions to a user in a container having a weight which, even when filled to a selected amount with fluid, is of a nature that the system can be manually held and manipulated.

Further it is an object of the subject system to provide a dispensing system which is collapsible subsequent to use for transportability in a minimum volume.

It is a further object of the subject dispensing system to provide a source of Epsom salt solution to a user which is portable and may be used without a bathtub and easily coupled or connected to a showerhead and which provides for easily adjustable heights and positions.

It is a further object of the subject dispensing system to provide a chemical salt composition which is portable, lightweight, collapsible and able to be easily transported.

It is a further object of the invention to provide a source of Epsom salt and essential oil solutions to a user's body which provides a more controllable concentration of the Epsom salt/essential oils to be applied to the user's body than would occur in a bath tub, or at least uses less Epsom salt to obtain a desired high concentration.

It is a further object of the subject system to provide a source of Epsom salt solution to increase magnesium intake to address magnesium deficiencies which has occurred in a user.

It is a further object of the subject system to provide a source of Epsom salt solutions to a user which allows for essential oils or other additives to be combined with or used in the place of an Epsom salt solution.

It is a further object of the subject system to allow a user to easily determine when the salt mixture has been dispensed entirely or almost entirely.

It is a further object of the subject system to enable users who do not have bathtubs to obtain benefits that are attributed to soaking in a salt water baths.

It is a further object of the subject system to allow the system to be easily transported and secured at different heights without requiring manual dexterity and strength related to manipulating mechanisms that are clamped to shower heads or which require installation of specialized shower heads.

It is a further object of system to provide a dispensing system which enables a salt composition and water mixture solution of a predetermined concentration to be imparted on a user at a predetermined concentration and flow rate and in a manner that disassociates the flow rate from the concentration. As opposed to known prior art, the system does not require replacement of a shower head and does not have to be securely attached to the showerhead, which requires a showerhead of a particular shape or contour. This is an advantage over the known prior art, since there are numerous showerhead designs that may be incompatible with a selected device that is designed to be affixed to, and/or form a watertight seal with, a showerhead.

It is a still further object of the subject dispensing system to provide a system which is easily removable from a showerhead or other supporting structure and used as a health accessory that may be carried by the user while on vacation, to the gym, or used at any other location where the user may wish to apply a controlled and concentrated salt solution.

A further object of the subject dispensing system is to provide a system which is structurally configured to be portable (rather than being securely fastened or realized within the actual structure of a showerhead) and enables the dispensing system to be easily transported to, and used at different locations without requiring time and effort to un-attach/reattach the dispensing system to a particular showerhead, and may be used with a wide variety of showerheads, or in some circumstances without any showerhead.

Another object of the subject dispensing system is to provide a dispensing system which does not require a fixed structural communication with, or otherwise fixed engagement with a showerhead and therefore is not restricted to a particular design of the showerhead. the subject system is provided with an adjustable fastening system such as an adjustable, flexible strap member which can be slid on/off an existing shower head or other supporting structure which obviates the need for a proximal end of the tubular container to rely upon an element that secures to a shower head in a watertight or other manner that requires gaskets and/or higher levels of compression.

Another object of the subject dispensing system is to provide a dispensing system which can be used by, and adapted for, persons of varying height including those who may not be tall enough to reach the showerhead or other supporting structure. Opposingly the subject dispensing system does not require the user be sufficiently tall (i.e., "showerhead height") to manually reach a mechanism attached at about the same height as the showerhead or other supporting structure for insertion of the salt composition and for adjusting the position of the device which is connected to the showerhead and further does not require that the user or person (such as an elderly person) possess the manual dexterity and strength required to firmly assemble or otherwise manipulate the separate components of known prior art systems during each use.

An additional object of the subject dispensing system is that the dispensing system uses a preselected concentration and volume of salt composition and water mixture solution. It allows the user to know when the salt has been fully depleted in contrast to solutions realized inside showerheads where a user may continue to apply water to their body after the salt has been depleted.

BRIEF DESCRIPTION OF THE DRAWINGS

FIG. 4 is an embodiment of the dispensing system which provides for a shelf having a port below the chemical salt composition chamber and in fluid communication with a conduit to a flow handle for passage of fluid there through;

DESCRIPTION OF THE PREFERRED EMBODIMENTS

Figure 6:
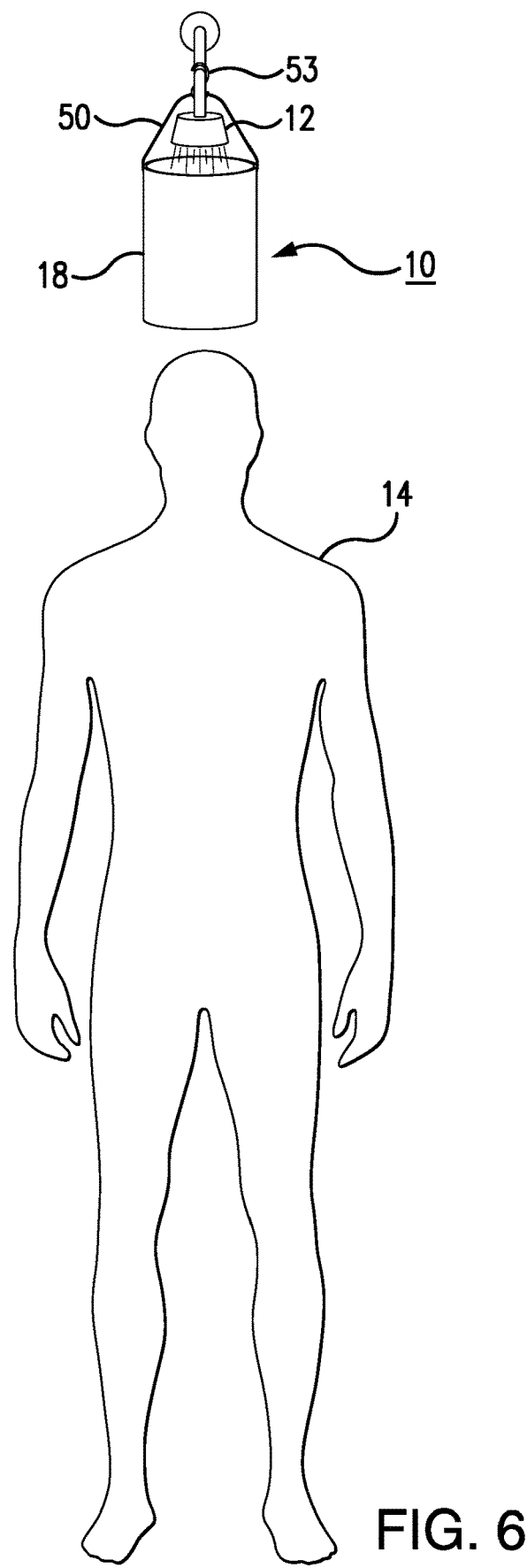
FIG. 6 is a schematic view of the system adapted to be mounted to a showerhead for passage of the solution to the user's body.

Referring now to FIGS. 1, 3, 6 and 7 there is shown a dispensing system 10 for controlled and selective dispensing of chemical salt compositions onto the human body 14. In overall concept, as shown in FIG. 6, dispensing system 10 may be mounted on a shower head 12 above user 14 and upon actuation of the shower head for dispensing water, such water flows into a chemical salt composition 16 which at least partially fills tubular container 18 as shown for example in FIGS. 1, 3, 4 and 9 to be further discussed in the following paragraphs.

In general, tubular container 18 is adapted to have inserted therein chemical salt composition 16 and possibly other essential oils which will have liquid passing there through for eventually striking the body of user 14 where some of the salt composition components will be absorbed into the body of user 14.

Figure 1:
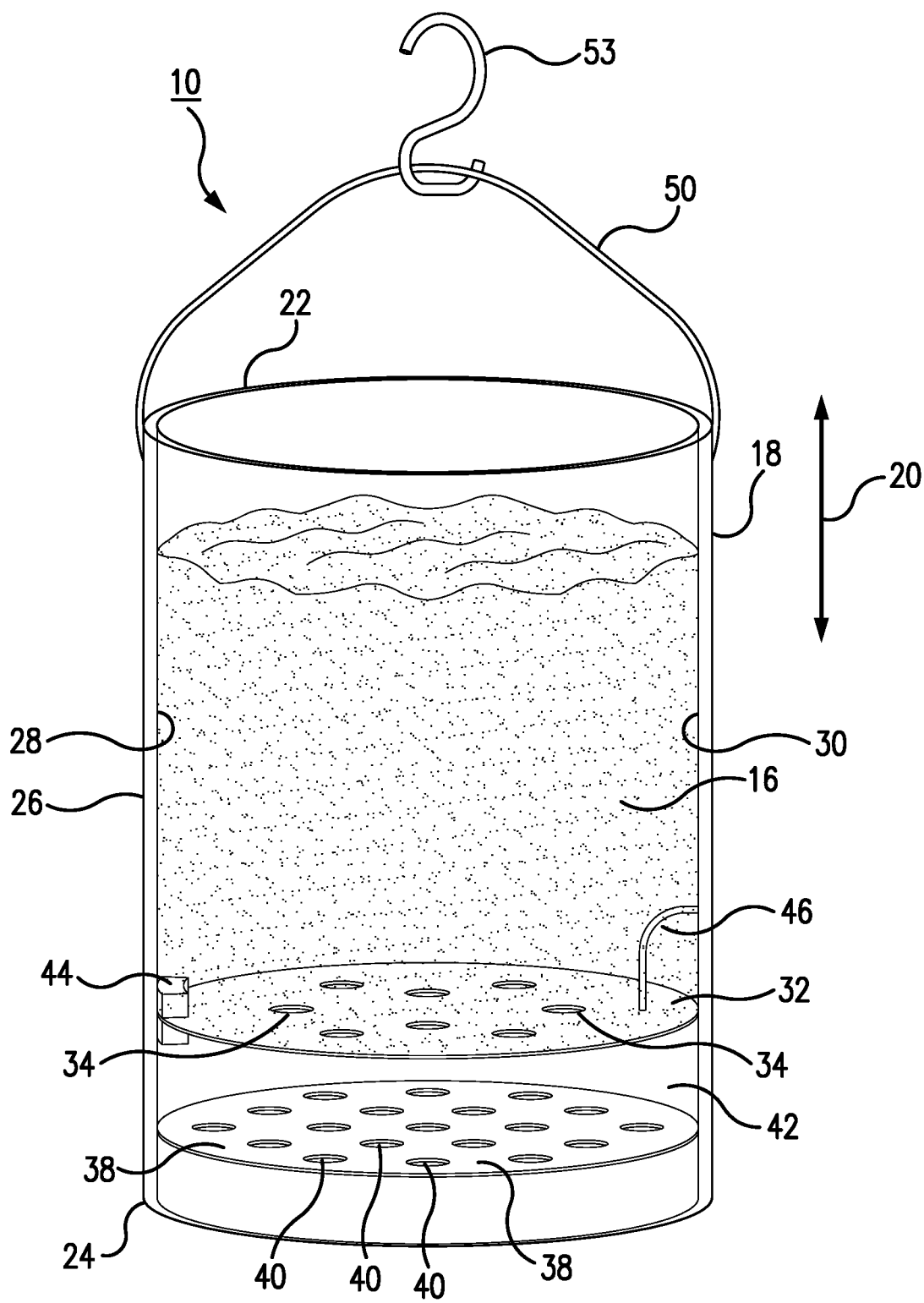
FIG. 1 is a schematic drawing showing a dispensing system having two vertically displaced sieve or shelf members beneath a chemical salt composition chamber containing the chemical salt composition.

Referring to FIG. 1, there is shown tubular container 18 ascending in vertical direction 20. Tubular container 18 includes proximal end 22 and distal end 24, where proximal end and distal ends 22 and 24 are on opposing ends of tubular container 18 when taken with respect to vertical direction 20. Tubular container 18 in certain embodiments may be formed of a somewhat flexible material such as silicone which has the ability of maintaining the semi-rigid tubular shape during use, but also may be collapsed prior to and subsequent to use in order to reduce the volume of the entire dispensing system to permit transportability in a minimum volume. Alternately tubular container 18 may be formed of a plastic polymer or other structural material which is lightweight in nature and can accept the load bearing of material contained within the tubular container 18.

As can be seen for example in FIG. 1, tubular container 18 is formed of a tubular side wall 26 extending in vertical direction 20 with a tubular container side wall inner surface 28. A first sieve or shelf member 32 is positioned and mounted in releasable contact with first tubular side wall inner surface 28. First shelf 32 is releasably mounted to the tubular container side wall inner surface 28 between the distal end 24 and the proximal end 22 of the tubular container 18. Releasable mounting of first shelf 32 may be effected through a number modes such as the insertion of first shelf member between a pair of vertically displaced lug members 44 formed on tubular sidewall inner surface at one transverse end of first shelf member 32, in combination with a tether 46 on an opposing transverse end of first shelf member 32. The tether 46 may be secured to both the tubular sidewall 26 and the first shelf member 32 on opposing ends respectively. In other aspects, as will be discussed in later paragraphs, shelf member may be mounted on a ring element which extends around the inner periphery of tubular container 18.

First sieve or shelf 32 has a plurality of through openings 34 passing through sieve 32 in substantially vertical direction 20 to permit the water activated chemical salt composition 16 to pass there through into mixing flow dispensing chamber 42. First sieve or shelf 32 may be fabricated from a plastic polymer and may be formed in particular from silicone. In general shelf 32 when formed of a silicone type polymer is formed of a more rigid or harder silicone than the sidewalls of tubular container 18 in order to maintain the structural shape of the tubular contain 18 when the first shelf 32 is mounted therein.

In this manner, chemical salt composition 16 may be maintained in salt composition chamber 30 and dispensed in a controlled manner through the first sieve through openings or holes 34. The salt composition chamber 30 is formed within said tubular container 18 between the first sieve member 32 and the proximal end 22 of the tubular container 18 for containing the chemical salt composition 16 as is seen in FIG. 1.

Dispensing system 10 permits the chemical salt composition 16 to be dispensed onto the body of the user 14 as depicted in FIG. 6. The salt composition chamber 30 permits the chemical salt composition 16 to be mixed with water and permits the user 14 to fill the chamber 30 to a point that the top of the chemical salt composition 16 is below the proximal end 22 of tubular container 18.

Tubular side walls 26 are generally formed in an extended tubular length along vertical direction 20. As previously detailed tubular container 18 may be formed of a flexible type of material such as silicone to allow reversible collapsing of tubular container 18. A silicone structure is generally found to be structurally stable and able to accept the force loading of the chemical salt composition 16. It is to be understood that tubular container 18 may be formed, at least in part, by a rigid material such as metal, alloy, any of the 7 types of plastic commonly recognized, a rubber material, steel, or some like material capable of accepting the force loads imparted thereto. In on preferred embodiment, tubular container 18 is formed of a flexible material which will allow tubular container 18 to be formed and collapsed into a compact volume during transportation. However, in other preferred embodiments the container is rigid to provide advantages of improved handling during use when it is filled with fluid.

In overall cross-sectional depiction, tubular container 18 may be circular, oval, or a parallelepiped contour for accepting the chemical salt composition 16.

In embodiments, tubular container 18 may have a contour which is cylindrical in nature and tapers from at least the proximal end 22 or distal end 24. Tapering of side walls 26 provide for a more directed application of the mixture of the chemical salt composition and water which is being applied to the body of the user 14. Dispensing system 10 in a cylinder type contour has a diameter at distal end 24 which is less than the diameter at proximal end 22 of tubular container 18 in a manner such that the diameter of tubular container 18 at distal end 24 may measure approximately 4.0 inches where the proximal end 22 of tubular container 18 may be in the area of 4.25 inches. This corresponds to a circumference for a cylindrically contoured tubular container 18 to approximate a circumference of 13.0 inches and the lower section or distal end point 24 has a circumference of approximately 12.5 inches. Overall vertical length of tubular container 18 generally approximates 7.0 inches to 9.0 inches. This type of configuration will provide for a tapering included angle of approximately 10.28 degrees.

Figure 2A:
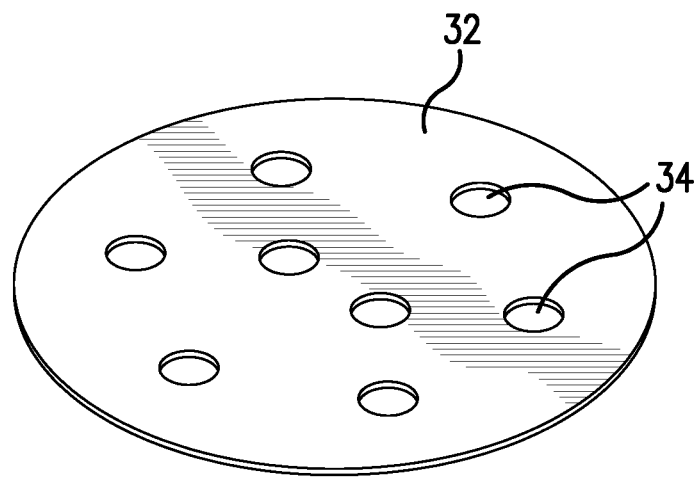
FIG. 2A is a schematic drawing showing a first sieve or shelf member having through holes.
Figure 2B:
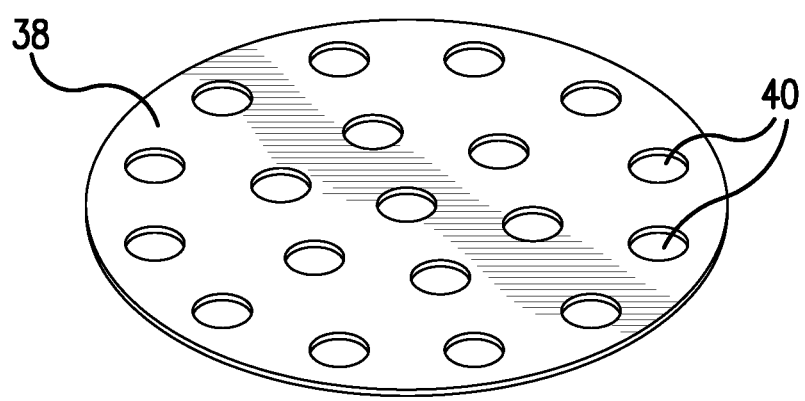
FIG. 2B is a schematic drawing of a second sieve or shelf member having a larger number of through openings than the first sieve member and mounted below the first sieve member as shown in FIG. 2A.
Figure 3:
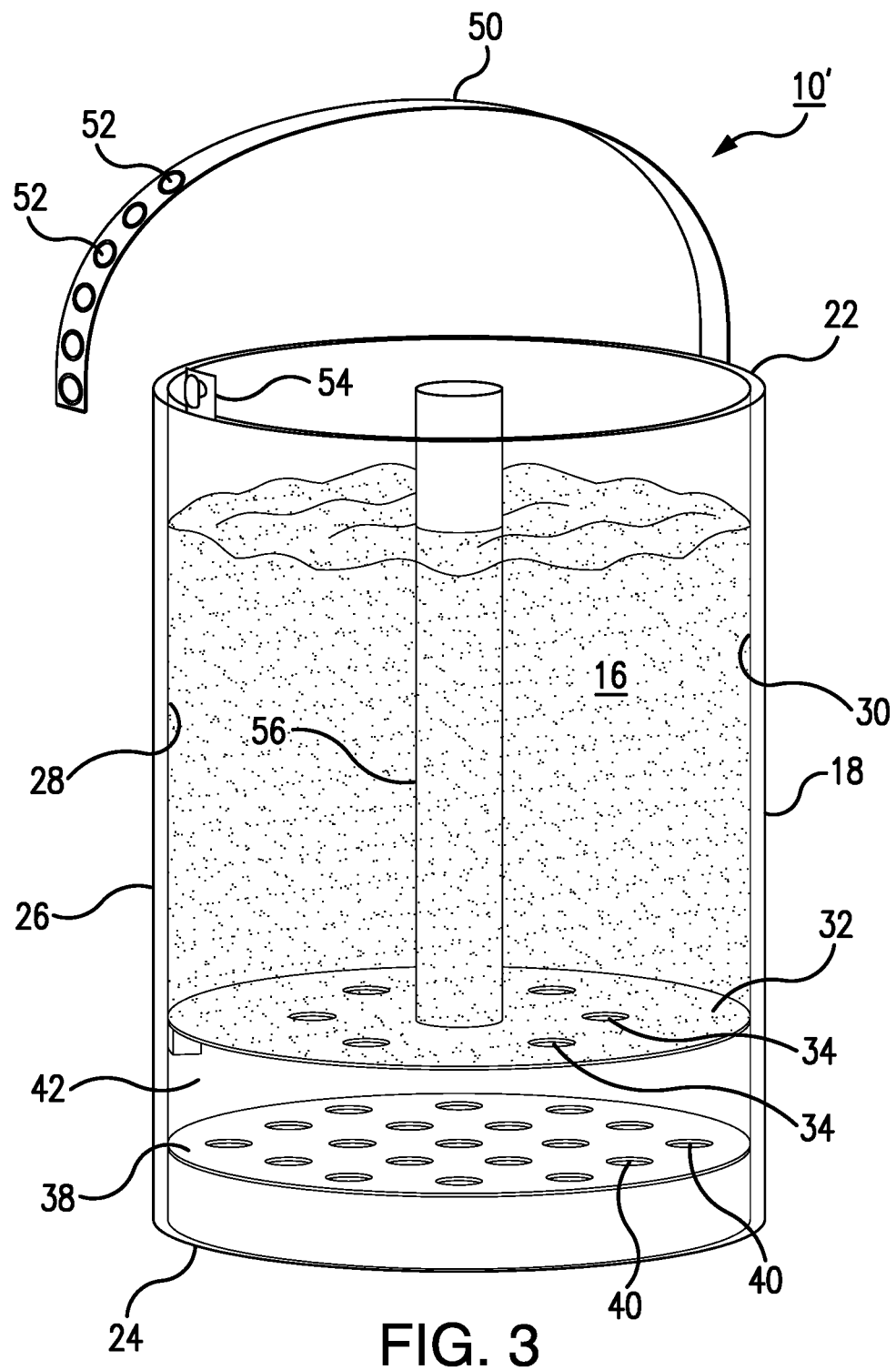
FIG. 3 is a schematic drawing of the chemical salt composition dispensing system showing a rod member attached to the first shelf or first sieve member for allowing removal or vertical displacement of the first sieve member with respect to a tubular container within which it is mounted, and a fastening member allowing the dispensing system to be mounted to a showerhead.

Turning now to FIGS. 1-3, dispensing system 10 may have a second sieve or shelf member 38 mounted to the inner surface of side wall 28 below the first sieve member 32. The first sieve member 32 and the second sieve member 38 define a mixing flow chamber 42 therebetween. Second sieve member 38 includes a plurality of second sieve through holes 40 for dispensing of the chemical salt composition and water mixture onto user 14. Second sieve or shelf member 38 may also be formed of a silicone polymer material or in the alternative may be formed of a more rigid material to further reinforce the structural contour of the tubular container 18 when in use.

The first sieve member 32, as is seen in FIG. 1, may be mounted between mounting lug members 44 on one side and possibly attached to the tubular side wall inner surface 28 through a connection tie or tether 46. Connection tie 46 may simply be a string or other type of cord like member which is attached to first sieve member 32 on one end and to tubular side wall inner surface 28 on an opposing end as is seen in FIG. 1.

In embodiments, both first sieve members 32 and second sieve member 38 are formed of a somewhat flexible material such as silicone. However, it is generally necessary that both sieve members 32 and 38 are formed of a material which is less flexible than the tubular side walls 26 in order to permit structural acceptance of the force loads applied when the chemical salt composition 16 is within salt composition chamber 30. In fact, second sieve member 38 may be formed of a rigid material such as plastic, metal or some other rigid material which will conform and maintain the tubular side walls 26 in a more rigid manner to accept the loads associated with chemical salt composition 16 subsequent to insertion into salt composition chamber 30.

Second sieve member 38 is mounted to tubular side wall inner surface 28 above tubular container distal end 24. Second sieve member 38 is thus mounted within tubular container 18 below first sieve member 32 and above distal end 24 of tubular container 18. As seen in FIG. 2, first sieve member 32 includes a plurality of first sieve member through hole openings 34 which are substantially sized to be equal to the second sieve member through holes 40. In one embodiment, the through openings 34 and 40 may be approximately 0.5 to 2 mm in diameter. It is important that the integer number of first sieve through openings 34 be less than the integer number of second sieve through openings 40. In this manner, the chemical salt composition and water mixture 16 will then trickle out slowly through the first sieve member 32 due to the fewer openings 34 in the first sieve member 32 with respect to the through openings 40 in the second sieve member 38. With the use of fewer and/or smaller holes or openings 34 in first sieve member 32 with respect to second sieve member 38, the water and chemical salt composition will have a longer period of time to remain in the salt composition chamber 30 and to allow further dissolving of the salt in the water. With the additional hole openings 40 in the second sieve member 38, the combination of the chemical salt composition and water is permitted to flow through the second sieve member 38 and provide an even distribution onto the user 14.

The dispensing system 10 may include a first shelf ring member 48 secured to the inner surface 28 of the tubular side wall 26 with the first shelf ring member 48 extending throughout the perimeter of the inner surface 28 of tubular sidewall 26.

Referring once again to FIG. 1, there is shown dispensing system 10 having a positioning member 50 secured and coupled to opposing laterally displaced ends of proximal end 22 where positioning member 50 is adapted to hang the tubular container 18 on a shower head 12 schematically shown in FIG. 6. Additionally, positioning member 50 includes a clip member 53 for mounting tubular container 18 in a releasable coupling to the shower head 12. As seen in FIG. 3, positioning member 50 may include a number of displaced positioning member openings 52 with fastening hook 54 coupled and securely mounted to proximal end 22 of tubular container 18.

In this manner, positioning member 50 may be mounted at differing heights from shower head 12 at the desirability of the user 14. In this manner, dispensing system 10' is height adjustable with respect the body of user 14 as required.

In this manner, with the displaced openings 52 formed through positioning member 50, such permits adjustability of height between shower head 12 and tubular container 18 in a simple and easy manner.

Positioning member 50 may be a strap formed of flexible plastic, textile or other like material not important to the system concept as herein described with the exception that the strap or positioning member 50 be able to accept the structural loads imparted by the weight of the chemical salt composition 16 within salt composition chamber 30 and not be chemically reactive with respect to the composition 16.

As shown in FIG. 3, dispensing system 10' may include rigid rod member 56 secured to first sieve or shelf member 32 on one end thereof. Securement of rigid rod member 56 to first sieve member 32 may be through bolting, adhesive securement or other like technique. First sieve rigid rod member 56 is fixed to the upper surface of first sieve member 32 and extends into chemical salt composition chamber 30 to permit first sieve member 32 to be vertically displaceable and allow removal or partial removal of first sieve member 32. In this manner, when user 14 wishes to remove some or all of chemical salt composition 16, the user 14 simply grasps the end of the rod 56 near proximal end 22 of tubular container 18 and pulls up on rod 56 for removal or partial displacement of first shelf member 32 with respect to tubular member 18.

Figure 4:
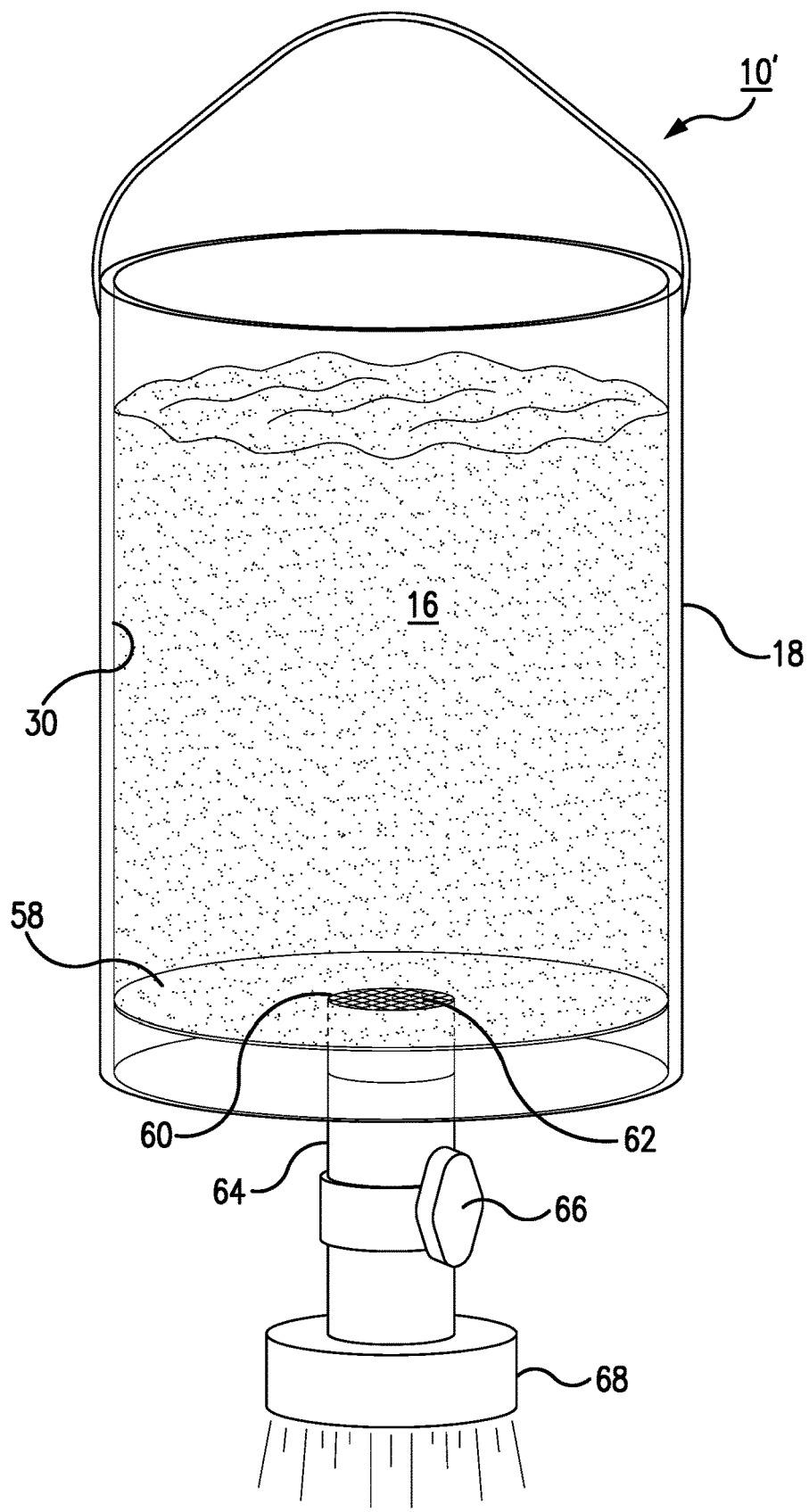

Referring now to FIG. 4, there is shown dispensing system 10" which has a singular disc member 58 mounted above distal end 24 of tubular container 18. Disc member 58 includes a central port area 60 defining a through opening of disc member 58. Central port member 60 may have a mesh covering 62 (or be realized as a substrate containing through holes) to allow flow distribution from salt composition chamber 30 into conduit 64 for passage through handle 68 having openings formed there through for distribution of the chemical salt composition and water mixture onto the user 14 (i.e. the bottom of the handle may be provided with a set of apertures that enable the fluid to be dispensed in an intended manner such as uniformly across the region defined by its circumference). Control valve 66 may be formed in the conduit 64 for permitting control of dispensing fluid including the rate of dispensing and complete halting of dispensing. In this manner, dispensing system 10" includes mixing/containment chamber 30 where chemical salt composition 16 and water are substantially mixed. In embodiments the chamber 30 is capable of storing between 2 and 15 cups of fluid to produce a fluid weight of between about 1 and 8 pounds (and less than about 10 pounds total), but more preferably holds about 5 cups of water and at least 0.5 cups of salt (i.e., 1 to 10 ratio). This embodiment shows the output port 60 formed on the shelf member or disc member 58 with the outflow port 60 being in fluid communication with the conduit 64 which terminates at a distal end in the handle 68 having holes passing there through which allows the mixture to pass onto the body of the user 14.

Control valve 66 may be one of a number of hand operated control valves which are commercially available. The control valve 66 is used to control fluid flow through conduit 64 by essentially varying the size of at least one flow passage through the conduit 64. By rotating the end member of the control valve 66 to a desired angle, the user is able to control the rate of fluid being dispensed (i.e. amount of liquid flowing to the handle 68 region over a selected interval).

Handle 68 may be a rubber or plastic ring formation with holes in the bottom for allowing the mixture to be dispensed over the cross-sectional area of the bottom of the handle 68. The regulator or control valve 66 is mounted intermediate the opposing ends of conduit 64 and can be regulated to terminate flow or provide a controlled amount of flow rate of the mixture.

Figure 7:
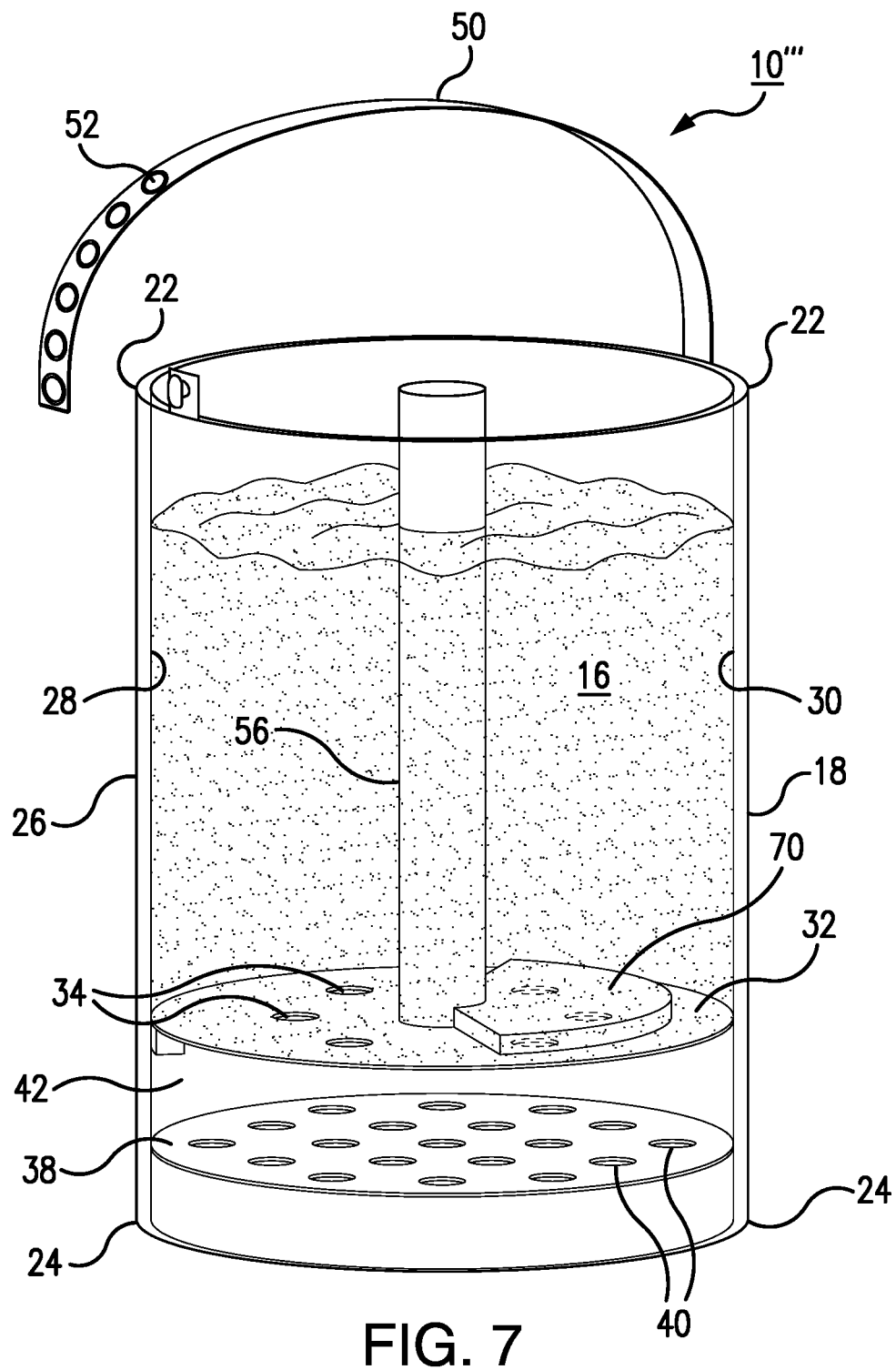
FIG. 7 is a schematic view of the chemical salt composition dispensing system which includes a control mechanism to open or close predetermined through openings in the first shelf member for controlling the flow rate through the first shelf member.

Referring now to FIG. 7, there is shown dispensing system 10''' which includes rod member 56 coupled to first sieve member 32 on one end thereof within tubular container 18 as previously discussed. In this embodiment, there is added flow control mechanism 70 which is realized in this embodiment as a slidably interfacing with an upper surface of first sieve or shelf member 32. The flow control mechanism 70 may be a sliding solid portion or element which is can be adjusted to cover one or more sets of the through openings 34 in order to control fluid flow through first sieve member 32 into chamber 42 and then through the openings 40 as previously described. In an embodiment, sets of holes are arranged with different densities upon the first sieve member 32 so that the flow control mechanism 70 will block a different number of holes as it is rotated, so that different flow rates will result.

In this manner, a predetermined number of first sieve through openings 34 can be opened for flow there through wherein the flow rate is controllable by the user 14.

Figure 5:
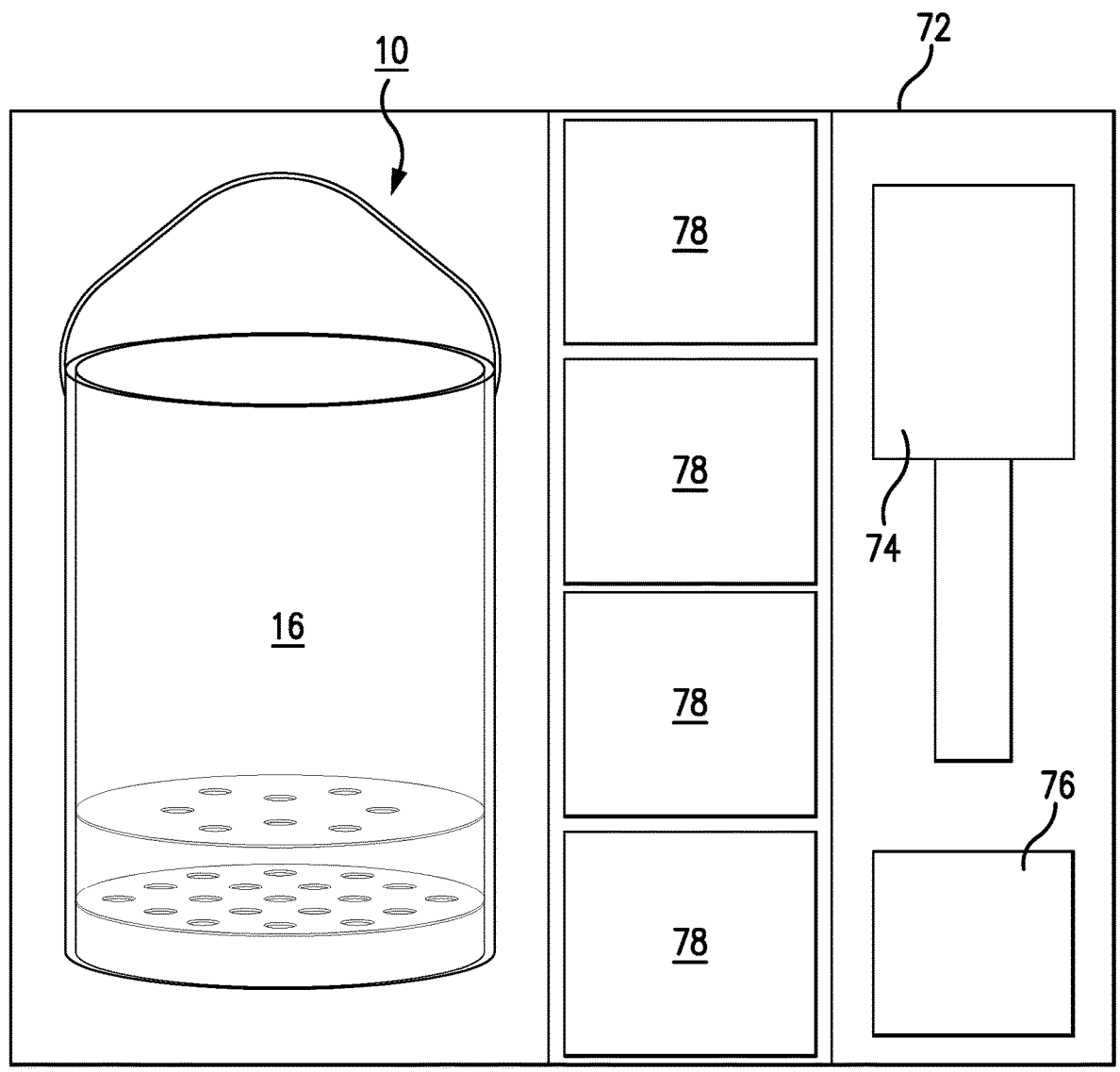
FIG. 5 is a schematic representation of a boxed kit which permits storage and transportation of a chemical salt composition system, a plurality of chemical salt composition packets, a brush and instructions for use.

Referring now to FIG. 5, there is shown schematically a kit for the chemical salt composition container dispensing system 10 wherein there is boxed a brush 74 and instruction manual 76, a plurality of chemical salt composition packets 78 and the dispensing system 10 as well as any other components of various embodiments of the system (e.g., caps, a tubular sieve, different base portion designs, various attachment clips and straps, essential oils or scented tinctures). The instruction manual may include tables with suggested amount of salt, water/fluid, and number of drops of essential oil, CBD, or other additive which is suggested in order to obtain desired solutions. The packets 78 may contain a measured amount of various chemical salt compositions appropriate for a single use. As an example, the dispensing system 10 is filled with approximately 945 ounces of water and each packet uses 94 ounces of salt providing substantially a one to ten concentration. It is known that transdermal application may be dependent upon a number of parameters such as time of application, strength/concentration of the chemical salt composition and other parameters including flow rate. The amount of composition within the composition packets is generally sized to permit evacuation of the mixing chamber to be within 1.0 to 4.0 minutes under normal shower flow rates of 1 to 2.5 gallons per minute. If the system is used with a pre-defined amount of fluid mixed with a predefined amount of salt then in an embodiment 45 ounces of water are used and the salt pack has 4.0 ounces of salt (e.g., 5.5 cups of fluid and 0.5 cups of salt). In this second embodiment, the same concentration of salt water is obtained as when fluid is provided from a shower head during use, but the method uses much less salt and water.

Brush 74 may be used for exfoliation which may provide advantages relating to increasing transdermal penetration of salt ions. Instruction manual 76 may be included in the boxed kit 72 to provide instructions to the user either in paper form or DVD or other electronic medium. In embodiments, the system of claim 10, realized as part of a kit which also includes additives selected to be at least one of: essential oils, fragrances, vitamins, lotions, medicinal substances such as Cannabidiol (CBD). The additives may obviously be provided in measured amounts that are appropriate for single use application to the fluid held in the container 18*a*.

Figure 8:
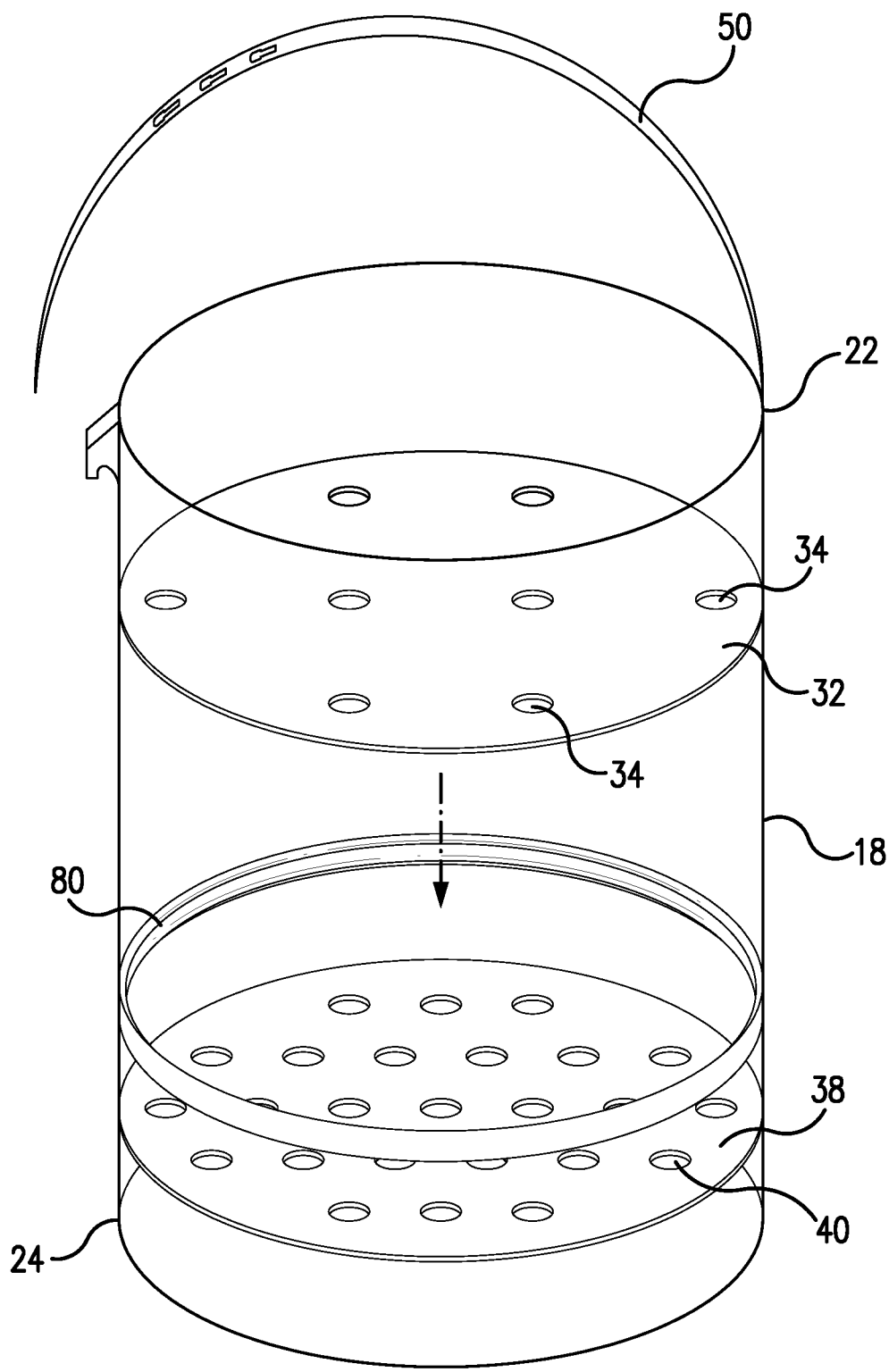
FIG. 8 is a schematic drawing showing a ring member extending around the periphery of an inner wall of the tubular container upon which the first shelf or sieve member is mounted; and, FIG. 9 is a partially cut-away schematic view of the dispensing system showing the first and second shelf members having an arcuate contour.

Referring to FIG. 8, there is depicted an embodiment of the dispensing system 10 where a mounting ring 80 is secured to the inner tubular sidewall inner surface for mounting thereon the first shelf 32. The mounting ring 80 may be formed in one piece formation with the tubular container 18 or otherwise attached through adhesive attachment, bolting or some like technique. First sieve or shelf member 32, may be inserted into tubular container 18 and mounted on mounting ring 80 to provide a structurally sufficient system to contain the composition 16.

Figure 9:
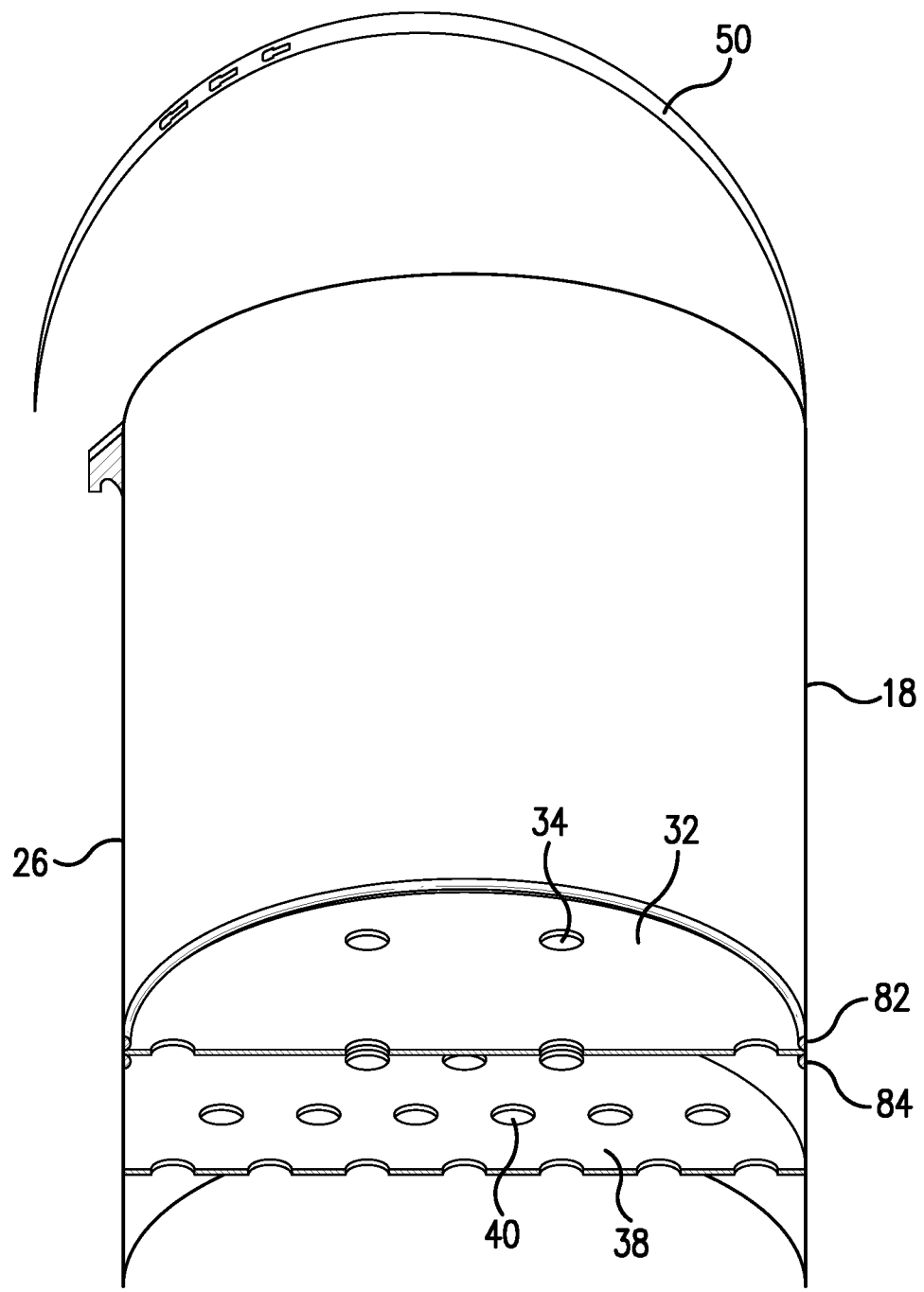

Referring to FIG. 9, there is depicted an embodiment where the first shelf 32 is deformed into an arcuate shape for mounting between either one or two ridges 82 and 84 which are located in a manner where the ridges 82 and 84 are able to capture the first shelf 32 therebetween. Since first shelf is somewhat flexible, it can be deformed when inserted into the ridges 82 and 84 to provide a compressive fore against the tubular sidewall 26 and add structural rigidity to the tubular container 18. Alternatively, there can be one ridge 82 extending around the periphery of tubular sidewall inner surface 28 where first shelf 32 is mounted thereon in a releasably fixed manner.

Figure 13A:
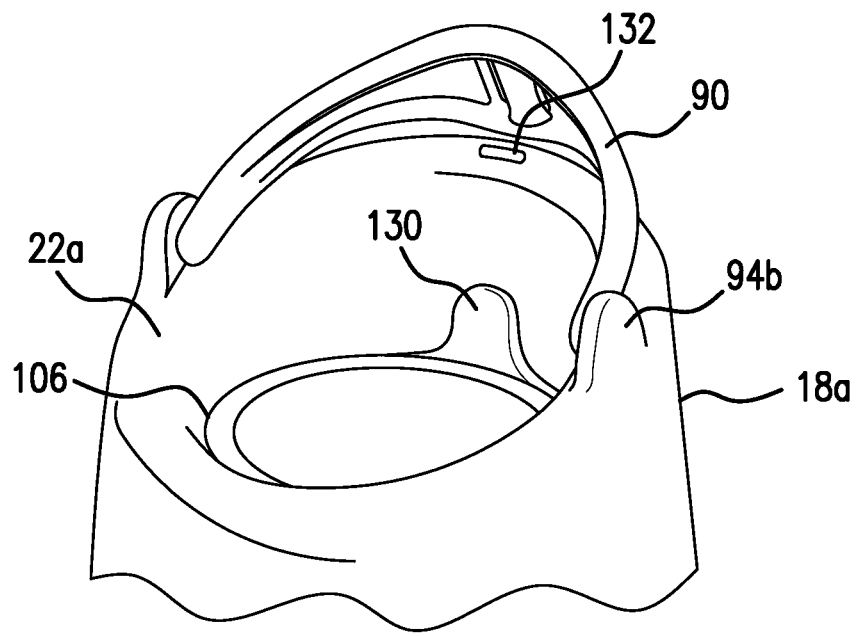
FIG. 13A, a perspective, partially cut-away schematic view of the sieve-like container mounted in the proximal end of the outer housing.
Figure 13B:
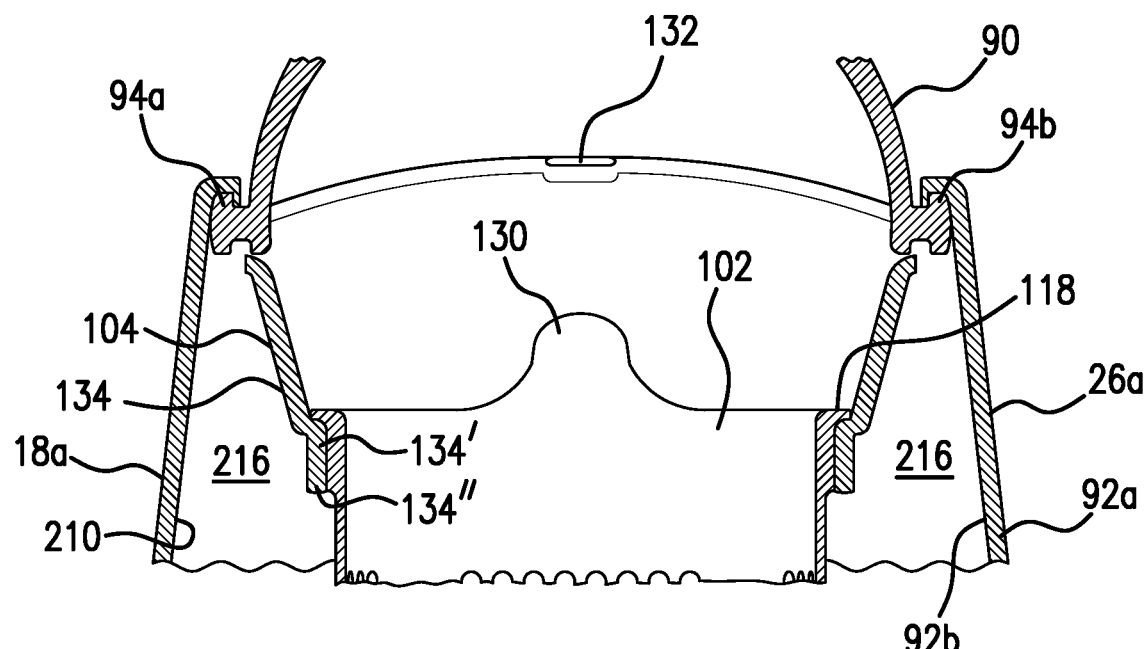
FIG. 13B is a cross-sectional and partially cut-away schematic view of the sieve-like container shown in FIG. 13A.
Figure 14B:
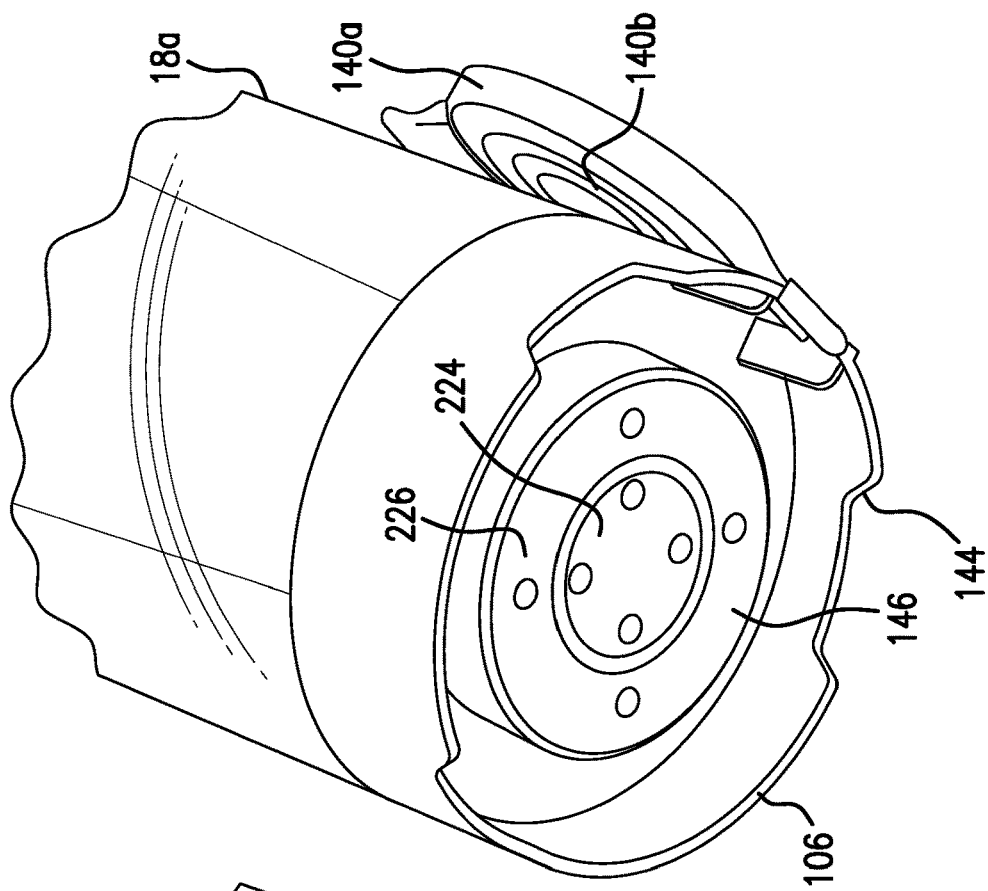
FIGS. 14a and 14b show a cap in a closed and open position.
Figure 14A:
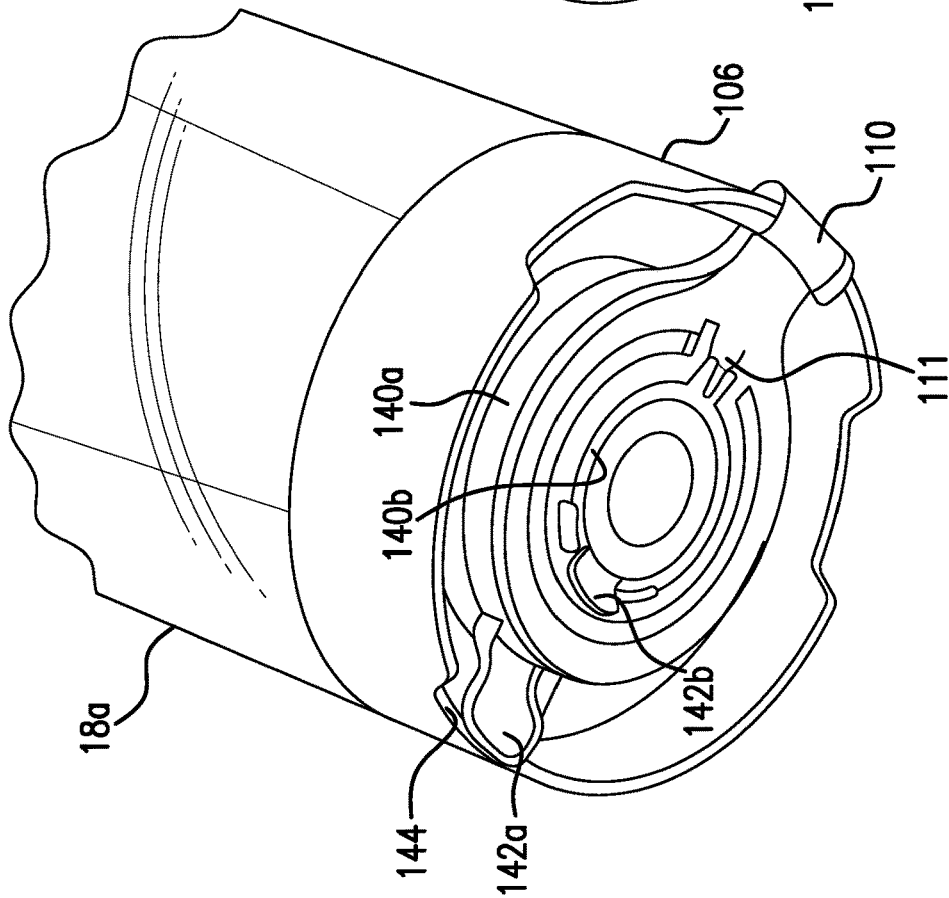
Figure 15B:
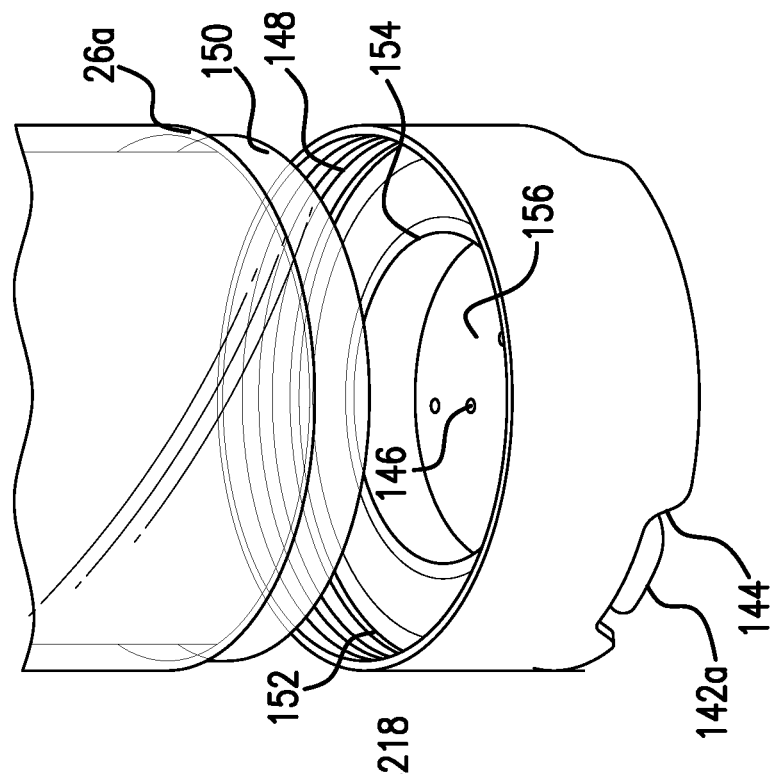
FIG. 15B is a perspective partially cut-away depiction of the outer housing and the separate base member where the inner and outer cap members are displaced from the base member to permit a maximum flow rate of the aqueous chemical salt composition from the outer housing.

FIGS. 10-15B show different embodiments of a dispensing system 10*a* In overall concept, the dispensing system 10*a* is operable to dispense a controlled and selected concentration of an aqueous chemical salt composition onto a user 14. As will be detailed in following paragraphs the dispensing system 10*a* includes an outer housing 18*a* having a proximal and a distal end with a base member 106 which may form a lower section of the outer housing 18*a* or be incorporated as a separate and distinct element as shown in FIGS. 14A-15B. The outer housing or container 18*a* defines an elongated tubular container which may be cylindrical, or oval in contour or further have a cross-sectional polygonal contour. A sieve member 102 is releasable to and insertable within the outer housing 18*a*. The sieve member 102 is adapted to contain a chemical salt composition which is mixed with a liquid to form the aqueous chemical composition which is dispensed to the user 14. A spatially adjustable positioning member 200, which may be a flexible strap which is releasably secured to a shower head or other supporting structure for positioning the outer housing 18*a* and the sieve member 102 to the shower head or other supporting member. A flow control mechanism as seen in FIGS. 15A-15B is connected to the base member 106 and is configured to permit manual operation by the user for controlling a flow rate of the aqueous chemical composition dispensed from the dispensing system 10*a* and the base member 106 onto the user.

Figure 10:
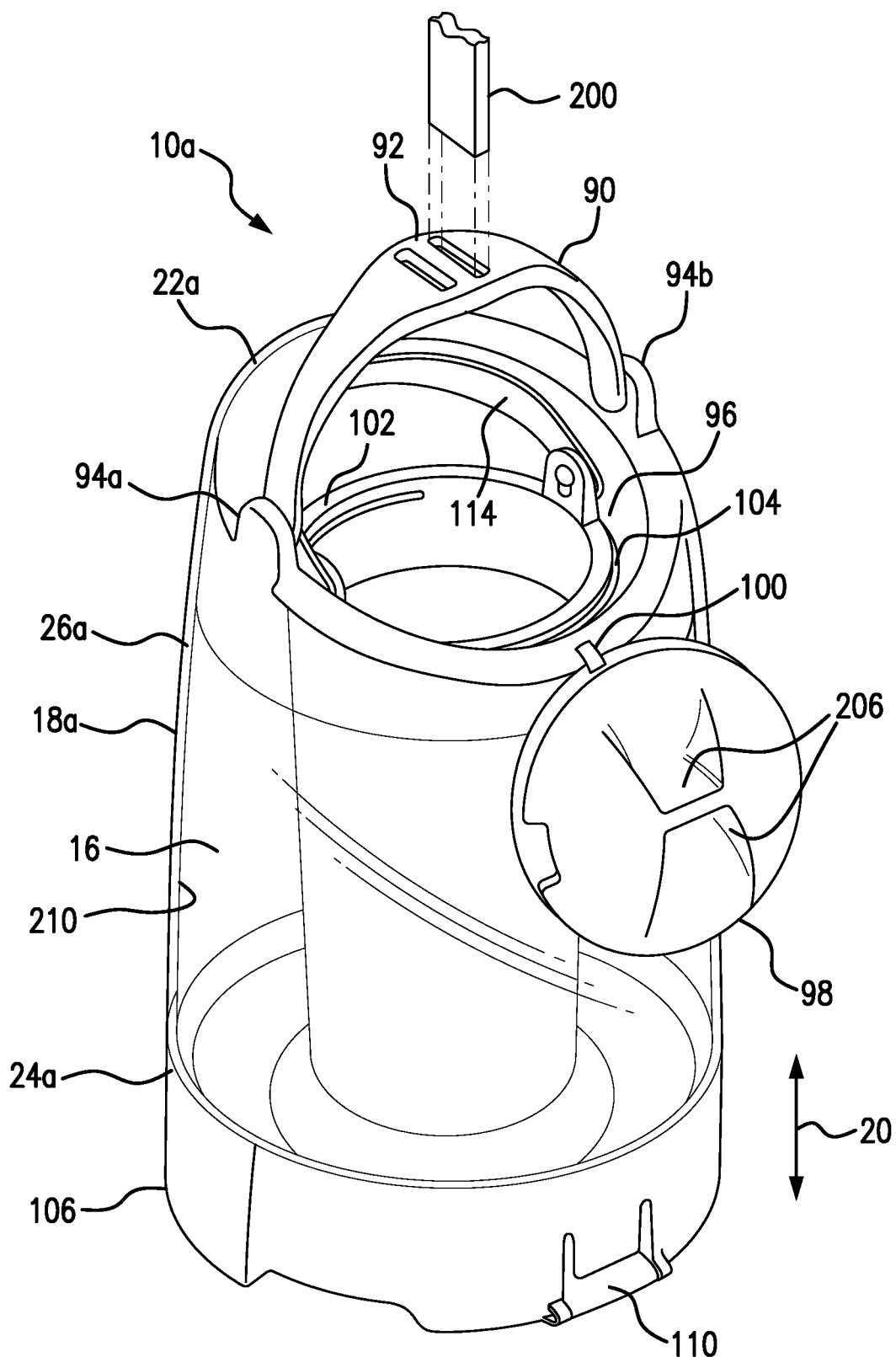
FIG. 10 is a perspective schematic view of an alternative embodiment of the dispensing system which includes an outer housing and an inner sieve-like container for containing a chemical salt composition.

Referring now in detail to FIG. 10 which is a perspective, schematic view of dispensing system 10*a* for controlled dispensing of selected concentrations and volumes of chemical salt compositions onto the human body 14. The dispensing system 10*a* may be configured to be secured in a releasable manner to a shower head, shower pole, shower curtain pole, or other stable support by way of a positioning mechanism 202 that may be attached directly to the tubular container or outer housing 18*a* or may be attached to a handle 90 which is connected to the outer housing 18*a*.

Dispensing system 10*a* includes outer housing 18*a* which includes a lower base member or housing lower section 106. In one form of dispensing system 10*a*, base member 106 defines a lower section of outer housing 18*a* which is part and parcel of outer housing 18*a* defining an outer housing 18*a* which is unitary with and forms a part of outer housing 18*a*. In another form of the subject dispensing system, as shown in FIGS. 14A-14B, base member 106 is a separate and distinct element with respect to outer housing 18*a* and is releasably attachable to outer housing 18*a*.

In one form positioning mechanism may be a handle 90 in combination with a flexible strap or band 200 which is threaded through a pair of through slits 92 and releasably attached to a support fixture such as a shower head. The strap member 200 is used to position the outer housing or tubular container or cylinder 18*a* above the user 14 or over a user's intended body part so that the salt mixture is dispensed thereupon.

Strap member 200 is sized to fit loosely through slits 92 and may be adjustable in overall length to accommodate proper positioning of dispensing system 10*a* at a selected distance between the user 14 (or users body part) and the shower head or other support structure. Flexible strap member 200 may be formed in one piece formation through use of overlapping hook and loop sections to permit adjustment of the length of strap member 200 thereby permitting the selective distance between user 14 and the support structure. Alternatively, strap member 200 may be formed in the manner of a belt with a belt buckle where the strap member 200 includes spaced apart through openings to permit adjustment of the overall length of strap member 200 in a manner well known in the art.

Handle 90 can be secured to the proximal or top end 22*a* of the outer housing or cylinder 18*a* in a fixed manner or in a manner that allows rotation of the handle 90 such as by being rotatably retained by handle fastener tabs 94*a* and 94*b* that are formed on the top of the outer housing or tubular container or cylinder 18*a*. Handle fastener tabs 94*a* and 94*b* include respective handle openings which have inserted therein respective lug members 204 which have substantially the same construction as lug members 204 shown in the perspective view of the sieve member 102 in FIG. 11A. The handle openings are sized to receive lug members 204 and have a diameter slightly larger than the diameters of lug members 204 in order to allow rotation of handle member 90 with respect to outer housing 18a to permit a certain amount of reduction in the overall volume of dispensing system 10a when not in use.

The proximal end 22a of the outer housing or container 18a defining an open end of outer housing 18a defining an aperture 96 that permits insert of the sieve member 102 and allows liquid to be inserted. Aperture 96 is configured to receive a cap member 98 to provide a physical seal and prevent spillage of any liquid or particulate matter contained within outer housing 18a.

Cap member 98 may be a threaded cap that operates with a threaded spout provided at the top or proximal end of the outer housing or cylinder 18a, or a threaded portion of an inner wall of outer housing 18a, or alternatively can be a cap 98 that is shaped to fit snuggly into the aperture 96. The cap member 98, in one embodiment may be secured to tubular container sidewall 26a through a strap that attaches cap member 98 to outer housing 18a. In another embodiment, outer housing 18a includes a notch 100 formed in tubular container sidewall 26a where cap member includes a cap lug which is insertable into notch 100 in friction constraint therewith to permit releasable attachment of cap member 98 to outer housing 18a. Cap member 98 further may include a pair of finger insert recesses 206 which permit a user to easily grasp cap member 98 and secure such to outer housing 18a as shown in FIG. 10, or to sieve member 102 as shown in FIG. 11A.

Figure 11A:
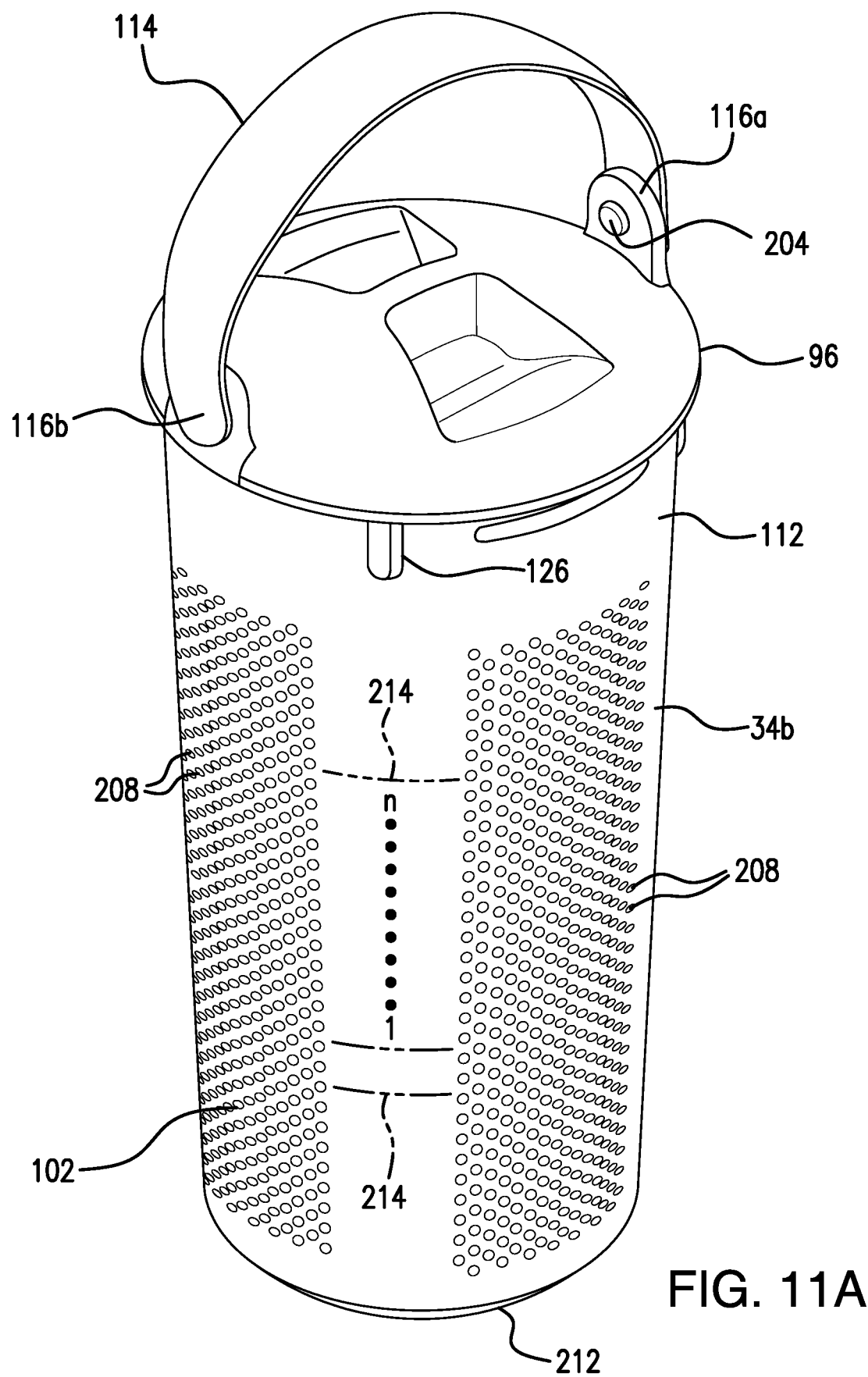
FIGS. 11A-11C is a perspective schematic views of a sieve-like container formed in cylindrical form having fluid transmitting openings.
Figure 11B:
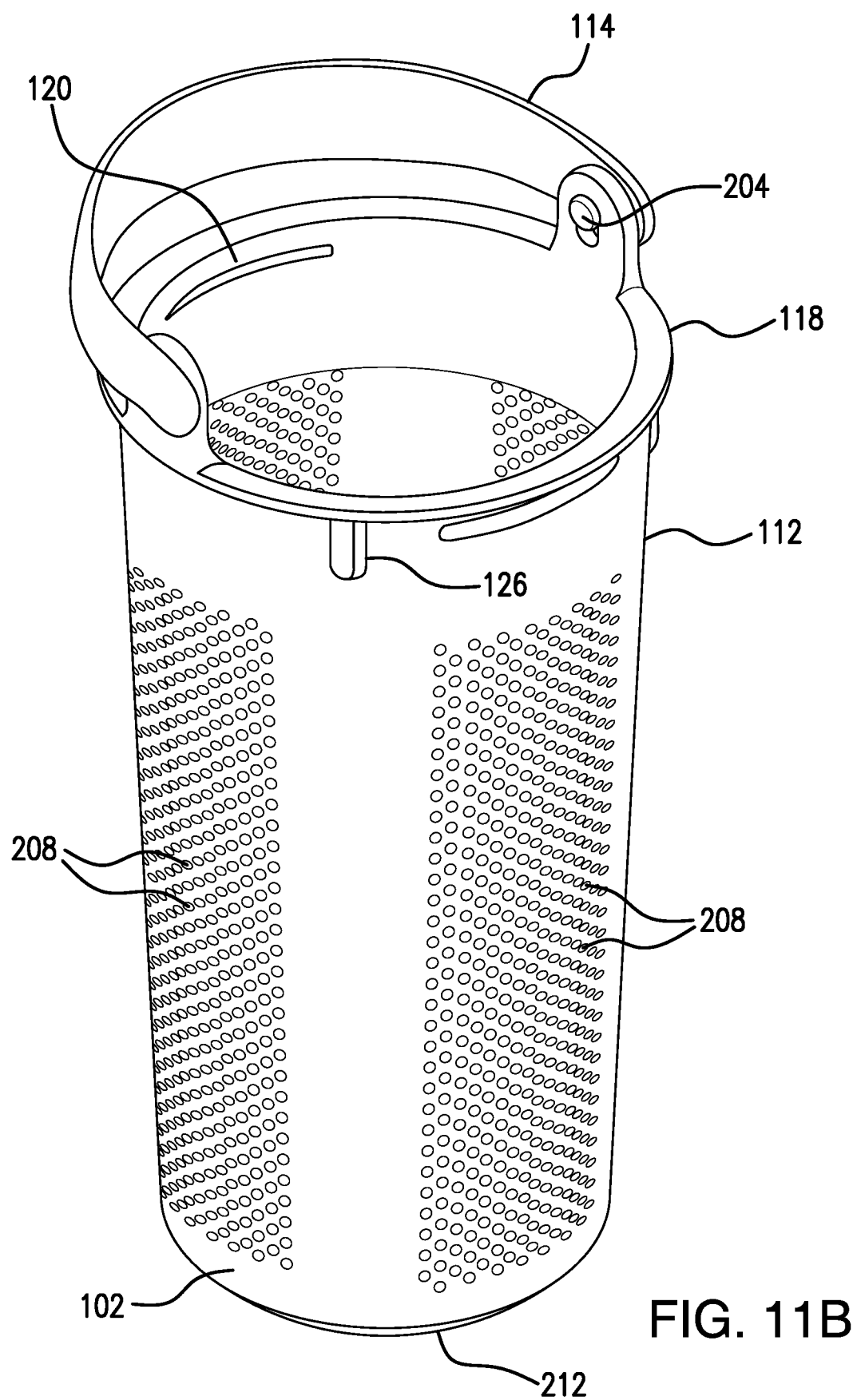

Referring now to FIGS. 11A and 11B, cap member 98 can be configured to be releasably secured to sieve member 102 which is mounted or resting on ridge 134 (seen in FIG. 13B) which is formed as a section of diagonal wall 104 of outer housing wall 26a of outer housing 18a. In this embodiment sieve member 102 includes flange 118 which is seen to interface and be mounted on ridge 134 of diagonal wall 104. In the embodiment shown on FIGS. 13A and 13B, sieve member 102 includes pull tabs 130 for simple release of sieve member 202 from outer housing 18a through aperture 96 which is seen in FIG. 10.

Sieve member 102 includes sieve sidewall 112 includes an array of sieve through openings which extend through sieve sidewall 112 as is seen in FIGS. 11A and 11B to permit the aqueous salt solution within sieve member 102 to flow through openings 208 into annularly formed chamber 210 formed between an outer surface of sieve member 102 and an inner surface of tubular sidewall 26a. In order to accommodate the annular chamber 210, the outer diameter of tubular sieve member 102 is generally less than the diameter of the inner surface of tubular wall member 26a as is seen in FIG. 10. In the embodiment shown in FIG. 11A, the tubular sieve member 102 with the openings or holes 208 passing through the sieve member sidewall 112 is provided with a sieve handle 114 that is attached to sieve handle fasteners 116a,116b. As an example, and not to limit the scope of the invention, sieve openings may be sized to have diameters approximating 1.5 mm.

Figure 11C:
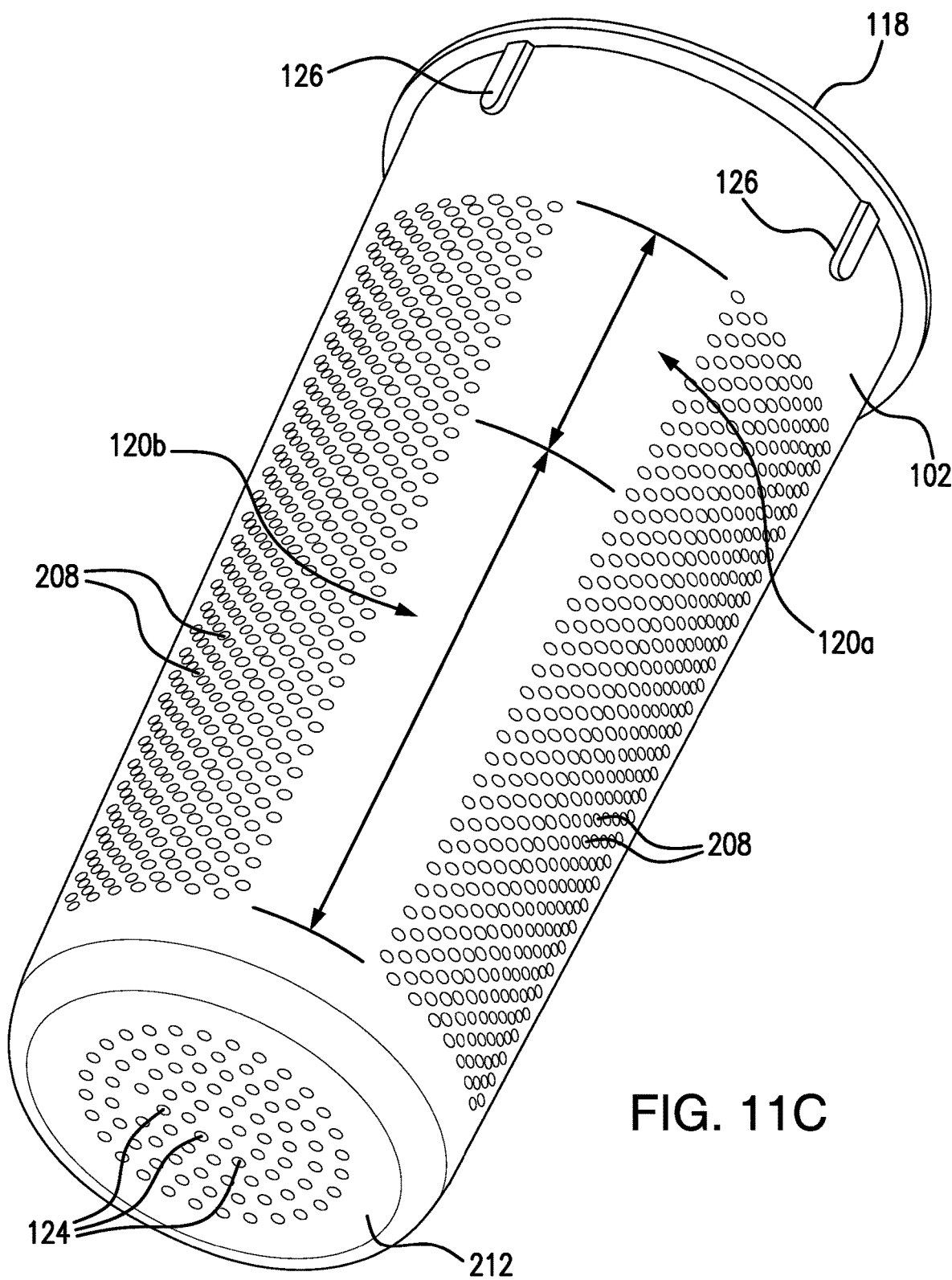
Figure 12:
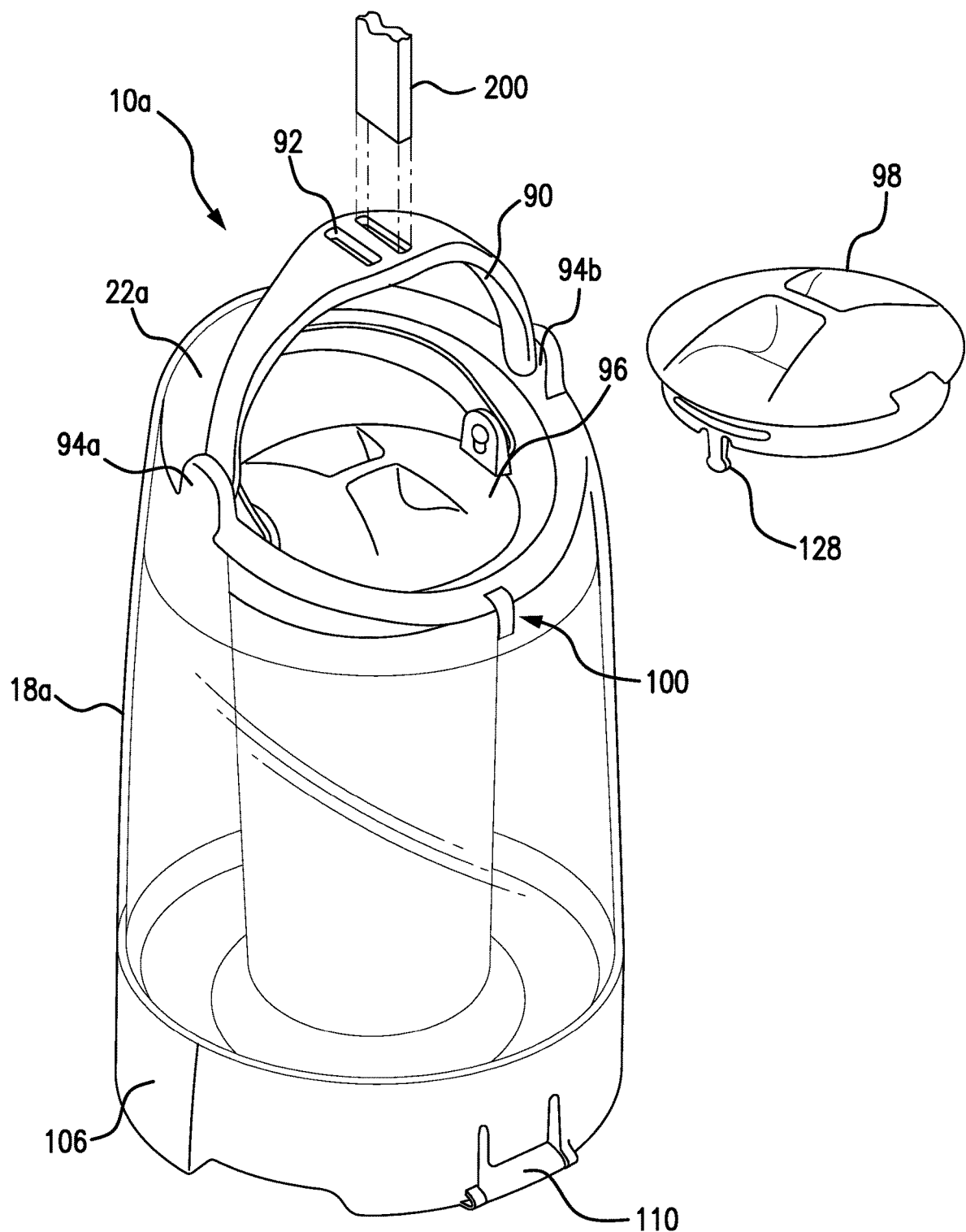
FIG. 12 is a perspective schematic view of an embodiment of the dispensing system showing cap members for both the sieve-like container and the outer housing.

As shown in FIG. 11C, sieve member 102 can be shaped to have a proximal ridge 118 that is shaped to engage a corresponding ridge of the aperture 96 on its lower side and the cap 98 on its top side. At least one through slit 120 is provided passing through the sieve sidewall 112 to engage the cap 98 and deter salt or fluid from leaving the cylinder during use. In alternative embodiments the sieve member 102 may have a threaded outer surface to engage with corresponding threads formed within diagonal sidewall 134 for threaded securement therebetween. Similarly, sieve member 102 may include threads on an inner surface to engage with corresponding threads on the cap 98. In this embodiment the sieve member 102 is threaded into the cylinder or outer housing 18a and then the cap 98 is threaded into a top section sieve member 102.

As further seen in FIG. 10, outer housing 18a may be formed of a lightweight material such as a plastic polymer composition or some like composition such as a silicone composition which may be flexible in nature and includes tubular sidewall 26a which is translucent or substantially transparent to allow the user to visually sense the amount of aqueous salt composition contained in dispensing system 10a at any time during the dispensing time interval. The material composition of outer housing 18a may be flexible in order to permit flexibility and allow collapsibility when dispensing system 10a is not in use.

Sieve member 102 shows sieve bottom wall 212 seen in FIG. 11C, which similar to the sieve member sidewall openings 208 in the sieve member sidewall 112 seen in FIGS. 11A and 11B, provides for an array of sieve bottom wall openings 124 to permit transmission therethrough of the salt composition aqueous solution.

Referring to FIGS. 13A-13B, there is seen sieve member 102 with a pull tab 130 attached to a proximal end for easy removal of sieve member 102 from the confines of outer housing 18a. Pull tab 130 may be formed in one piece formation with sieve member 102 or may be otherwise attached thereto. Drainage opening 132 is formed through a proximal surface of outer housing 18a in fluid communication with annular formed chamber 210 shown in FIG. 13B to permit release of any aqueous chemical composition from inner housing 18a and aid in the cleaning of dispensing system 10a subsequent to use. A flexible stopper formed of a rubber composition or like material may be inserted in drainage opening to maintain a closed annular chamber during use of dispensing system 10a and removed subsequent to use for cleaning purposes.

FIG. 13B, is directed to one manner of mounting sieve member within outer housing 18a where sieve member is mounted to an interior diagonal wall of outer housing 18a. Sieve member 102 and outer housing 18a extend substantially in vertical direction 20 when in use. In this embodiment, sieve flange 118 is sized to interface with and be mounted to diagonal wall ridge 134'. Sieve flange has an outer diameter larger than an inner diameter of the lower section 134" of diagonal wall 134. In this manner, when in the vertical position of dispensing system 10a, sieve member 102 is maintained in releasable constraint to outer housing 18a. Alternately, a proximal section of sieve member 102 may be threaded to receive a complementary threaded section or diagonal wall 134 to provide another mechanism for mounting and releasably securing sieve member 102 to outer housing 18a.

As in the case for the outer housing 18a, sieve member 102 may be formed of a composition which is formed of a plastic polymer, silicone composition or some like composition which may be transparent or substantially translucent to visualize the chemical salt composition contained within sieve member 102. Further as was the case for outer housing 18a, sieve member 102 may be flexible in nature to allow collapsibility when dispensing system 18a is not in use. Additionally, the outer wall of sieve member 102 may be formed with a means for determining the amount of chemical salt composition remaining in sieve member 102 which may be in the form of indicia 1 . . . n (as shown in FIG. 11A) or in the form of arcuately contoured bands 214 spaced apart in vertical direction 20 which may be used to allow the user to visualize the amount of chemical salt composition that will be used during the dispensing period of time.

In order to maintain sieve member 102 in a relatively fixed relation to outer housing 18a, guide lug members 126 are provided on an outer wall of sieve member 102 as shown in FIGS. 11A-11C to maintain sieve member 102 in fixed rotational and vertical displacement with respect to outer housing 18a. Guide lug members 126 are adapted to be received within corresponding recesses formed within an inner wall of outer housing 18a and maintain a relatively fixed positioning of the sieve member 102 when taken with respect to the outer housing 18a.

In one form of the embodiments as described, fluid flow from the base member can be adjustably controlled by a flow controller mechanism similar in nature to that shown in the embodiment provided in FIG. 4 which essentially consists of a fluid flow egress conduit 64, a control valve 66 and an end spray cap 68. In such an embodiment, conduit 64 is in fluid communication with a lower surface of base member 102. The conduit has mounted thereon a control valve 66 which may be manually operated to restrict or alternatively increase the fluid flow from base member 106 through conduit 63 and into spray cannister 68 for dispensing the fluid onto the user. The control valve 66 may be one of many commercially available valve mechanisms well known in the art. Alternatively flow control may be obtained through a flexible set of tubes in fluid communication with the base member 106 which can be used in conjunction with clip members which can be used for constricting the flexible tubes by some predetermined amount or completely blocking fluid flow to the spray cannister 68.

In an alternate embodiment, fluid flow can be controlled directly from base member 106 through the use of end caps which are coupled to a lower base plate 156 of base member 106 as is seen in FIGS. 14A-14B and FIGS. 15A-15B to be further described in following paragraphs.

Figure 15A:
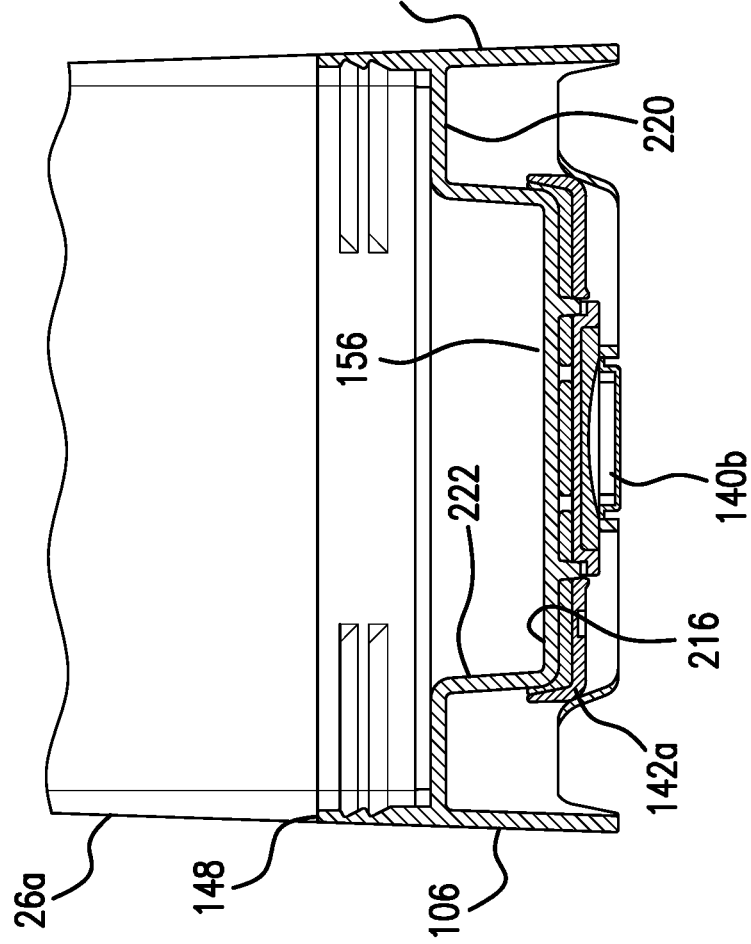
FIG. 15A is a perspective partially cut-away depiction of the outer housing and a separate base member showing a pair of inner and outer cap members where the cap members are positioned to stop flow from the outer chamber defining a closed position.

Referring now to FIGS. 10, 12, 14a-14b and 15A-15B, there is shown base member 106 which coupled to outer housing 18a at a distal end section 24a of outer housing 18a. As is seen in one form of dispensing system 10a, base member 106 and outer housing 18a may be formed in one piece formation, or as seen in FIGS. 15A-15B in releasable coupling each to the other.

Base member 106, shown FIGS. 15A-15B, includes base sidewall 218 which interfaces with and is releasably secured to outer housing or tubular sidewall 26a. Base sidewall 218 is formed in one piece formation with base upper wall 220 which provides a platform for tubular sidewall 26a of outer housing 18a. base inner wall 222 is generally formed in one-piece formation with base member lower plate 156 to form a base member recess or mixing chamber 216 for receiving aqueous salt solution being fluidly transmitted through sieve member sidewall openings 208 into annularly formed chamber 210 shown in FIGS. 10 and 13B as well as through sieve member bottom openings 124 shown in FIG. 11C. Base member lower plate 156 further includes base lower plate through openings 146 for transmitting the aqueous salt solution being collected in the base member mixing chamber 216 to the user.

Base member 106, may be mounted to outer housing 18a as part of a lower section of outer housing 18a when taken as one molded piece, can be mounted through a force fit friction coupling between the respective members, or other like mounting configuration which permits the user to couple and decouple base member 106 from outer housing 18a.

Base member 106 coupling and decoupling from outer housing 18a permits the user to couple/decouple the respective members in order to simplify the cleaning process between uses or otherwise store the respective members in a reduced volume configuration. Base member 106 may be formed of a lightweight material composition such as a plastic polymer composition or other like composition which is compatible with the structure of outer housing 18a. Generally, base member 106 may be formed of a closed cell plastic polymer composition which is substantially rigid in nature to allow coupling and decoupling from outer housing 18a as well as to support a structure capable of having a flow control mechanism attached thereto as will be discussed in following paragraphs associated with FIGS. 14A-14B.

Referring back to FIGS. 15A-15B, there is shown one releasable coupling arrangement between base member 106 and outer housing 18a where tubular sidewall 26a has a lower threaded section 150 which interfaces with base member threaded section 148 to permit releasable fastening of base member 106 to outer housing 18a. A gasket 152 is provided throughout the periphery of base member ridge 154 to provide a sealing or leak proof element between outer housing 18a and base member 106. Gasket 152 may be in the form of an O-ring sandwiched between base member ridge and a distal end of outer housing or tubular container 18a. In this manner aqueous salt solution is maintained internal to outer housing 18a and directed into base member mixing chamber 216.

FIGS. 14A-14B are partially cut-away schematic drawings of dispensing system 10a showing a flow control embodiment of dispensing system 10a using a cap system which employs at least two caps, namely first or outer cap 140a and second or inner cap 140b. In general, cap 140a has a diameter larger than cap 140b with caps 140a and 140b being coupled each to the other as will be further detailed in following paragraphs.

As can be seen in FIG. 14B, lower base plate 156 of the base member 106, includes at least two lower base plate regions, namely first lower base plate region 224 and second lower base plate region 226. Each of the regions include a selected number of openings 146 which determine the flow rate of the aqueous chemical salt solution being transmitted from outer housing 18a to the user 14. The flow rate is determined by the positioning of the outer cap member 140a and the inner cap member 140b each with respect to the other and further with respect to base lower plate 156. Outer cap member 140a is sized to cover both first and second lower base plate regions 224 and 226 when in a closed position. Outer cap member 140a therefore has a diameter substantially equal to or larger than a diameter of lower base plate member 156 or at least of sufficient diameter to cover both regions 224 and 226. Inner cap member 140b is sized to cover the second lower base plate region when in a closed position. Thus, inner cap member 140b has a diameter substantially equal to or larger than the diameter of lower base plate member first region 224.

As can be seen in FIG. 14A, both the outer cap 140a and the inner cap 140b are in a "closed" position covering both base plate 156 first and second regions 224/226 to block any aqueous chemical composition from exiting dispensing system 10a. FIG. 14B shows the inner/outer caps 140b/140a in a fully "open" position where the aqueous chemical salt composition is free to pass through all the openings 146 in both the first and second regions 224 and 226 of the lower base plate member 156.

Outer cap member 140a is rotatably mounted to outer housing 18a by outer cap hinge 110 as shown in FIG. 14A.

Outer cap hinge 110 may be formed of a plastic connection extending from a peripheral surface of outer cap member 140a and secured to in one-piece formation to the base member 106 sidewall or some like hinge coupling system which are commercially well known. In this manner outer cap member 140a may be rotated with respect to a plane of lower base member plate 156. As seen, outer cap member 140a includes outer cap member tab 142a attached to a periphery of Outer cap member 140a. Outer cap member tab 142a is sized to extend (at least slightly) from the sidewall of base member 106 in order to allow the user a finger hold on outer cap tab 142a to allow grasping of the outer cap tab member 142a and permit the user to displace outer cap member 140a into and out of contact with lower base plate member 156. Outer cap member tab member 142a is further sized to be insertable through base member recess 144 shown in both FIGS. 14A and 14B. Alternatively, outer cap member 140a may be fabricated as a separate element with respect to outer housing 18a and sized to be releasably attached to a periphery of outer housing 18a through a snap fitting or force fitting.

Inner cap member 140b is rotatably mounted to outer cap member 140a by inner cap hinge 111 as is seen in FIG. 14A. Inner cap member 140b is further releasably coupled to outer cap member 140a by a snap fitting or in some like manner to permit opening/closing of inner cap member 140b with respect to outer cap member 140a. Inner cap hinge 111 may be formed in one-piece construction with respect to outer cap member 140a and inner cap member 140b, which may be in some embodiments a flexible strap like element joining outer cap member 140a to inner cap member 14b. Alternatively, inner cap member 140b and outer cap member 140a can be two separate and distinct elements where inner cap member 140b is forcibly be fit onto outer cap member 140a by a force fitting and maintained in place by a friction fit coupling. Inner cap member 142a includes inner cap member tab 142b, as shown in FIG. 14A, which similar in operation to outer cap member 142a, allows the user to easily displace inner cap member 140b from outer cap member 140a.

Thus, dispensing system 10a is able to control the quantity of fluid passing to the user, by adjusting the dispensing system 10a to operate in transmission of the aqueous fluid salt composition in a closed, intermediate fluid flow condition, or a maximum fluid flow condition. When both the inner cap member 142b is secured in overlapping position to outer cap member 142a and outer cap member 142a is secured to outer housing 18a, as shown in FIG. 14A, there is no transmission of aqueous fluid salt composition to the user or person. When both the outer cap member 142a and the inner cap member 142b are in an open condition, as seen in FIG. 14B, aqueous chemical salt composition flows through openings 146 in both the first and second regions 224 and 226 of lower base member plate 156 providing a maximum fluid flow transmission to the user. When the outer cap member 142a is in releasable securement with outer housing 18a and inner cap member 142b is displaced from a fixed securement to outer cap member 142a, an intermediate flow rate is achieved since only the openings 146 in the second region of lower base member plate 156 allow for fluid transmission therethrough, resulting in an intermediate flow rate during a specific time interval. The cap members may engage with the outer housing 18a or each to the other in a manner other than a hinge design such as through complementary grooves, snap members and like mechanisms which provide releasable securement.

As shown in FIG. 11C, the sieve member 102 contains the bottom surface with through holes 124. Markings to show how much salt is contained within the sieve such as can be visually shown by use of color, texture, or breaks in sets of the through holes 208. As an example, the top set of holes stops in a region 120a associated with a first measurement, while a lower region 120b is associated with measurement of a different amount. For example, the upper region is associated with 1 cup of salt composition and the lower region 120b associated with a half cup of salt composition. These markings can also be provided on the outer housing 18a or tubular cylinder 18 to measure the amount of fluid being therein Referring back to FIG. 12 there is shown an embodiment of the system 10a in which the sieve member 102 is inserted in the aperture 96 of the outer housing 18a and sieve cap 96 is secured to provide a watertight seal or at least to deter fluid from leaving the container 18a. The tab 128 is formed in the cap 98 so that it can be attached to the cylinder 18a such as by insert into the notch 100 when dispensing system 10a is not in use. Alternatively, the cap 98 may be provided with a strap that secures it to the system (e.g. the handle 90 or other system component) so that it is not misplaced.

In an embodiment, the base member 106 is configured with the set of holes 146 (e.g., 4 to 30 holes) that are of sufficient number and size to cause the salt mixture to flow only due to gravity assist during a predetermined time interval. For example, the time interval may be between 1 and 10 minutes. Additionally, at least 1 cap 140a, 14b is configured to be connected to the base member 106 to adjust the amount of fluid that can flow from the set of holes or openings 146 in both first and second regions 224 and 226 or only through second region 226. For example, if cap 140a is attached to the base 106 and cap 140b is rotated outward to allow fluid to flow from the base member holes or through openings 146, then the flow rate would be decreased by a selected amount (e.g., 30-50%) compared to what occurs when both cap members 140a, 140b are rotated to their open positions as is shown in FIG. 14B. Rather than requiring 1-10 minutes for the fluid mixture to be fully dispensed from the container, the interval may be extended to 2-20 minutes dependent on the positioning of cap members 140a and 140b.

FIG. 15A shows the embodiment in which the base 106 is formed with a threaded annular wall 150 that engages the cylinder's threaded annular wall 148. The gasket 152 is provided to improve the seal between the base 106 and the cylinder 26a. The base member 106 contains the ridge 154 and a lower plate with the openings or holes 146 to allow fluid to flow therethrough.

In overall concept and referring to FIGS. 10-15B, the subject system provides for a system to dispense controlled and selected concentrations of a chemical salt composition which in many instances is an aqueous mixture of a salt composition and water providing to a user some therapeutic value. The system 10a includes an outer housing 18a having a base member 106 with the outer housing 18a defining an elongated tubular container extending in a vertical direction 20. The outer housing has a proximal end 22a and a distal end 24a.

A sieve member 102 is adapted to be releasably insertable within the outer housing 18a and is configured to contain a pre-selected amount of a chemical salt for eventually forming an aqueous chemical composition to be dispensed to the person or user. In order to accommodate users of differing heights, a spatially adjustable positioning mechanism 200, 90 is coupled to the outer housing 18a and is adapted to be flexibly secured to an installation supporting structure which may in many instances be a shower head. The positioning mechanism 90, 200 permits users of differing heights to adjust the system 10a at selective heights with respect to the supporting structure for ease of use.

System 10a further includes a flow control mechanism 140a, 140b, 156 connected to the base member 106. The flow control mechanism 106 is configured to manually operated by the user to control the flow rate of the aqueous chemical composition dispensed from the base member 106 onto the user.

In embodiments, the chemical salt composition 16 is created that at least partially fills the sieve member 102 which is shown for example in FIGS. 10, 11A-11C and 12. In embodiments, the tubular container 18a is adapted to allow for controlled mixing, retaining, and dispensing of a chemical salt composition 16 and possibly other mixtures such as essential oils or scents. The system allows for the specified solution to be applied in a controlled manner to one or more areas of a user's body 14.

As has been discussed in previous paragraphs, outer housing 18a may be formed of a plastic like composition for purposes of providing a light weight system 10a for easy transport by the user. Outer housing 18a further may be translucent or otherwise substantially transparent to permit the user to view the salt composition and the aqueous chemical composition within the outer housing 18a at any time before, during and after the dispensing of the aqueous chemical composition. In some embodiments of the subject system 10a, the outer housing 10a may have measuring indicia formed on or within an outer sidewall 26a to allow the user to view the amount of aqueous chemical composition within outer housing 18a and/or the remaining salt composition within sieve member 102. Similarly, sieve member 102, which may be formed as a tubular container having a cross-sectional circular or polygonal contour, may include indicia or other marking type elements formed within or on an outer surface of a sidewall to allow the user to view the salt composition within sieve member 102. Sieve member 102, similar to outer housing 18a, may be formed of a lightweight, substantially transparent or translucent material such as a closed cell plastic composition.

As further discussed in previous paragraphs, the base member 106 may be joined to the outer housing 10a in a variety of coupling manners. In one embodiment, both outer housing 18a and base member 106 may be formed as a singular one-piece element which can be attained in a molding process. In a number of embodiments, the outer housing 18a and the base member 106 are separate and distinct elements of system 10a which can be joined each to the other through a threaded connection or force fitting to permit friction securement and allow detachability of the separate elements 18a and 106.

In embodiments a tubular container 18a is configured to hold between 2 cups and 2 gallons of fluid, and more preferably about three/fourths of a gallon, and even more preferably between about 4-6 cups with 5 cups resulting in about 2.5 pounds in weight of water, which is likely to be suitable even for individuals who lack strength in upper body or manual grip.

In embodiments, the outer housing or tubular container 18a proximal end 22a has an aperture 96 that is configured with to receive a cap 98 that is releasably secured to the outer housing to deter fluid from exiting from the proximal end during transportation or during use. Additionally, the cap 98, may be configured to be secured to the top of a sieve member 102, which fits inside the aperture 96. The sieve member 102, is formed with an annular wall 112 having holes 24b and a handle 114 that is rotatably attached to two handle fastener arms 116a, 116b that are positioned on the proximal end of the sieve 102. The sieve 102 may be formed to be about one-third the volume of the container 18a and is of a length that extends from the aperture 96 on the proximal side of the container 18a to the base 106 of the container. The distal end of the sieve 102 may extend to be just above the base ridge 154, or may be of sufficient length to reside below the region of the ridge 154. If the sieve member 102 is formed so that a bottom region of the sieve member 102 occupies the space within the ridge 154, then water is biased to flow into the sieve prior to exiting through the set of holes 146. The sieve member 102 may be formed to secure to the cap 98 in various manners. For example, at least one slit 120 near the top of the sieve 102 can engage a flap of the cap 98 to removably secure the cap 98 in place after the sieve is inserted into the container. The sieve 102 can be configured to have at least one (or two) guide members 126 on its upper region near the ridge 118 that correspond to indentations in the aperture 96 to cause the sieve to be oriented in an intended manner when it is placed inside of the container 18a. Accordingly, the aperture 96 formed within the proximal end 22a of the container 18a is provided with at least one groove to receive the at least one guide 126 of the sieve 102.

In embodiments, the container 18a and base 106 is formed to hold about 4.5 cups of water and the sieve is formed to hold about 1.5 cups salt, and the concentration of the fluid dispensed by the container 18a has a pre-determine, user selected, concentration with a ratio of between 1 to 2, 1 to 3, 1 to 4, or 1 to 5 parts salt to water. The total amount of both salt and water used to provide the mixture is selected by a user and is a defined volume that is independent from the rate of flow of fluid from the container 18a. Importantly, the invention allows users to obtain strong concentrations of saltwater solutions, including saturated and supersaturated mixtures. High concentrations of saltwater can allow the user to abrade their skin with the resulting high-concentration mixtures.

The Environmental Protection Agency (EPA) estimates that the standard shower heads use 2.5 gallons of water per minute. Since there are 16 cups in 1 gallon, and 2.5 gallons comprises 40 cups of water, attempting to provide the same concentration from a shower would require 5.71 (40/7) cups of salt instead of 1. Further, known prior art cited is generally not designed to hold 5.71 cups of salt (or even 1 cup of salt) near a showerhead. Additionally, a standard bathtub holds 42 gallons of water and there are 16 cups to a gallon yielding 672 cups. Assuming, conservatively that a person only filled the bathtub half-way, this would require 672/2=336 cups of water. In order to then obtain a 1 to 7 ratio during, for example an Epsom salt bath where the bather would be required to pour in 48 cups (336×0.14) of salt, which would be extremely expensive and unpractical.

It is to be understood that although the preferred embodiment of the subject dispensing system is directed to dispensing controlled and selective amounts of the chemical salt compositions detailed above, the particular composition may include salt compositions, essential oils, bath pellets, scented and unscented soap, as well as soap powder and like compositions. Other types of additives such as aromatic oils and medication are contemplated by the subject dispensing system.

It is to be further understood that the tubular container in another embodiment of the subject dispensing system, may take the form of a porous bag which contains the salt composition or other substance to be applied to the body of the user. The bag may be formed of a mesh like textile or other material composition which allows the contained composition, after being impinged upon by water emitted from the shower head, to mix with and be at least partially dissolved prior to impinging on the user's body. The particular composition of the bag is not important to the inventive concept with exception that the material used be non-reactive with respect to the chemical composition within the bag. This embodiment further envisages a porous first bag at least partially filled with the composition to be applied to the user's body and a second porous bag within which the first bag is at least partially inserted. Both bags may be attached to the shower head by a releasable hook, or other fastening device which have been previously described. With this embodiment a more controlled application of the composition within the first bag can be applied to the user's body.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. System for dispensing controlled and selected concentrations of chemical salt compositions adaptable for use with a shower head, comprising:
    an outer housing having a base member, said outer housing defining an elongated tubular container extending in a vertical direction and having a proximal end and a distal end, and wherein said proximal end of said elongated tubular container is formed with an aperture in the proximal end of the elongated tubular container for receiving water;
    a sieve member releasably attached to and insertable within said outer housing defining a vertically directed elongated sieve wall member adapted for containing a chemical salt composition having an array of sieve member openings for transmission of said chemical salt composition therethrough into an annular chamber formed between said sieve wall member and said outer housing for reacting with water introduced through the aperture in the proximal end of the tubular container to form an aqueous chemical composition;
    a spatially adjustable positioning member coupled to said outer housing and adapted to be flexibly secured to the shower head for positioning said outer housing and said sieve member at a predetermined and adjustable distance between a user and said shower head, wherein said proximal end of said elongated tubular container is displaced from said shower head; and,
    a flow control mechanism connected to said base member and configured to be manually operated by a user for controlling a flow rate of said aqueous chemical composition dispensed from said base member and onto a person.

2. The system as recited in claim 1 wherein said chemical composition is an aqueous mixture of said chemical salt composition and said water.

3. The system as recited in claim 1 wherein said base member includes a base member sidewall and a base plate member forming a mixing chamber for said aqueous chemical composition, said base plate member having a plurality of openings for passage therethrough of said aqueous chemical composition.

4. The system of claim 3 wherein the number and aperture size of the openings is adjusted so that the interval required to drain the container of fluid is between 1 and 10 minutes.

5. The system as recited in claim 1 wherein said outer housing and said base member are shaped to engage with each other and fixedly couple each to the other in one piece formation.

6. The system as recited in claim 1 wherein said outer housing and said base member are releasably detachable each from the other.

7. The system as recited in claim 6 including a gasket formed on an inner wall surface of said base member for contiguous and continuous contact with the distal end of said outer housing for preventing leakage of said aqueous chemical composition external said base member.

8. The system as recited in claim 7 wherein said outer housing and said base member are threadedly secured to each other in a reversible manner.

9. The system as recited in claim 7 wherein said outer housing and said base member are force fit each to the other.

10. The system as recited in claim 1 wherein said outer housing includes at least a portion of which is transparent or translucent for permitting visualization of said sieve member.

11. The system as recited in claim 1 wherein said outer housing is formed of a plastic composition.

12. The system as recited in claim 1 wherein said outer housing includes an inner wall section extending from the proximal end of said outer housing having a ledge member formed at a distal end of said inner wall section for mounting said sieve member thereon.

13. The system as recited in claim 12 wherein said sieve member includes a sieve flange formed on a proximal end of said sieve member for releasably mounting said sieve member on said outer housing ledge member.

14. The system as recited in claim 12 wherein said sieve member includes at least one pull tab member extending from a proximal end of said sieve member to permit removal of said sieve member internal to said outer housing.

15. The system as recited in claim 1 wherein said sieve member includes a plurality of through openings formed through a sieve sidewall and a sieve bottom wall for permitting passage therethrough of said aqueous chemical composition.

16. The system as recited in claim 15 wherein said sieve member includes means for determining an amount of the chemical salt composition contained within said sieve member, whereby the concentration of the aqueous solution may be adjusted.

17. The system as recited in claim 16 wherein said means for determining the amount of the chemical salt composition includes a plurality of spaced apart indicia formed on the sieve sidewall of said sieve member extending throughout at least a portion of said sidewall of said sieve member.

18. The system as recited in claim 16 wherein said means for determining the amount of the chemical salt composition includes at least one visual indicia provided on a periphery of the sieve sidewall of said sieve member for providing measurement.

19. The system as recited in claim 1 wherein said flow control mechanism includes a first flow control cap member rotatably coupled to a distal end of said base member for blocking a first predetermined number of through openings formed through a base plate of said base member when said first flow control cap member is in a first rotated position and opening said first predetermined number of through openings when said first flow control cap member is displaced to a second rotated position.

20. The system as recited in claim 19 wherein said first flow control cap member is mounted to the distal end of said base member by a hinge.

21. The system as recited in claim 19 including a second flow control cap member mounted on and rotatably coupled to said first control cap member for blocking a second predetermined number of through openings formed through said base plate of said base member when said second flow control cap member is in a first position and opening said second predetermined number of through openings when said second flow control cap member is displaced to a second rotated position.

22. The system as recited in claim 21 wherein said second flow control cap member is hingedly secured to said first flow control cap member.

23. The system as recited in claim 1 including a housing cap member displaceably secured to an outer housing sidewall for being displaceable to (a) a first position to close the proximal end of said outer housing and (b) a second position to open the proximal end of said outer housing.

24. The system as recited in claim 23 wherein said housing cap member is hingedly coupled to said outer housing sidewall.

25. The system as recited in claim 1 wherein the proximal end is configured with an opening configured for receiving a cap to deter fluid from leaving the container after the container has been filled through the opening.

26. The system of claim 1 wherein the tubular container is configured to hold between 2 and 10 cups of fluid.

27. The system of claim 1 wherein the sieve is shaped to hold at least 0.5 cups of said salt composition.

28. The system of claim 1, realized as part of a kit which also includes additives selected to be least one of: essential oils, fragrances, vitamins, lotions, medicinal substances such as Cannabidiol (CBD).

29. The system as recited in claim 1 wherein said outer housing is made of a flexible material that allows the outer housing to be collapsible.

\* \* \* \* \*